US008691850B2

(12) United States Patent
Ergüden et al.

(10) Patent No.: US 8,691,850 B2
(45) Date of Patent: Apr. 8, 2014

(54) SUBSTITUTED PHENYLAMINOTHIAZOLES AND USE THEREOF

(75) Inventors: Jens-Kerim Ergüden, Wüfrath (DE); Gunter Karig, Köln (DE); Ulrich Rosentreter, Wuppertal (DE); Barbara Albrecht, Wülfrath (DE); Kerstin Henninger, Wuppertal (DE); Joachim Hütter, Wuppertal (DE); Nicole Diedrichs, Velbert (DE); Peter Nell, Wuppertal (DE); Sabine Arndt, Dortmund (DE); Walter Hübsch, Wuppertal (DE); Andreas Knorr, Erkrath (DE); Karl-Heinz Schlemmer, Wuppertal (DE); Dirk Brohm, Herdecke (DE)

(73) Assignee: Bayer Intellectual Property GmbH, Monheim (DE)

( * ) Notice: Subject to any disclaimer, the term of this patent is extended or adjusted under 35 U.S.C. 154(b) by 1162 days.

(21) Appl. No.: 11/661,820

(22) PCT Filed: Aug. 30, 2005

(86) PCT No.: PCT/EP2005/009316
§ 371 (c)(1),
(2), (4) Date: Mar. 10, 2008

(87) PCT Pub. No.: WO2006/027142
PCT Pub. Date: Mar. 16, 2006

(65) Prior Publication Data
US 2008/0269300 A1 Oct. 30, 2008

(30) Foreign Application Priority Data
Sep. 3, 2004 (DE) .......................... 10 2004 042 607

(51) Int. Cl.
A61K 31/4436 (2006.01)
C07D 417/12 (2006.01)

(52) U.S. Cl.
USPC ...................................... 514/342; 546/270.7

(58) Field of Classification Search
USPC ....................................... 546/270.7; 514/342
See application file for complete search history.

(56) References Cited

U.S. PATENT DOCUMENTS

| | | | |
|---|---|---|---|
| 5,889,002 A | 3/1999 | Nielsen et al. |
| 6,191,280 B1 | 2/2001 | Hamprecht et al. |
| 6,632,823 B1 | 10/2003 | Vernier et al. |
| 6,693,102 B2 | 2/2004 | Stasch et al. |
| 6,706,717 B2 | 3/2004 | Barrish |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter |
| 7,129,255 B2 | 10/2006 | Rosentreter et al. |
| 7,135,486 B1 | 11/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 2001/0027196 A1 | 10/2001 | Borroni et al. |
| 2003/0232860 A1 | 12/2003 | Harada |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschi et al. |
| 2005/0250774 A1 | 11/2005 | Ono et al. |
| 2006/0154969 A1 | 7/2006 | Rosentreter |
| 2006/0264432 A1 | 11/2006 | Rosentreter |
| 2007/0213372 A1 | 9/2007 | Rosentreter et al. |
| 2010/0022544 A1 | 1/2010 | Nell et al. |
| 2010/0069363 A1 | 3/2010 | Nell et al. |
| 2010/0093728 A1 | 4/2010 | Nell et al. |
| 2010/0197609 A1 | 8/2010 | Vakalopoulos et al. |
| 2011/0130377 A1 | 6/2011 | Nell et al. |
| 2011/0207698 A1 | 8/2011 | Meibom et al. |
| 2011/0294718 A1 | 12/2011 | Lerchen et al. |
| 2011/0294719 A1 | 12/2011 | Lerchen et al. |

FOREIGN PATENT DOCUMENTS

| | | |
|---|---|---|
| EP | 0 608 565 A1 | 12/1993 |
| JP | 09-132529 | 5/1997 |
| JP | 10-324687 | 12/1998 |

(Continued)

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
Yu et al., "Physical characterization of, etc.," PSTT, vl. 1(3), 118-127 (1998).*
Caruso et al., "Adenosine signaling, etc.," Expert opin. Ther. Targets (2013) 17(7), 761-772.*
Daines et al., "Intraocular Adenosine, etc.," Journal of Ocular Pharmacology and Therapeutics. 19(2), 2003, 113-119.*
Karmouty-Quintana et al., "The A2B adenosine, etc.," The FASEB Journal, 26, 2012 2546-2557.*
Avila, et al.: A1-, A2A- and A3-subtype adenosine receptors modulate intraocular pressure in the mouse, British Journal of Pharmacology, 2001, 134:241-245.
Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

(Continued)

Primary Examiner — Patricia L Morris
(74) Attorney, Agent, or Firm — Karen B. King; Thomas C. Blankinship

(57) ABSTRACT

The present application relates to novel phenylaminothiazole derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

4 Claims, No Drawings

(56) References Cited

FOREIGN PATENT DOCUMENTS

| JP | 2003-183254 | 7/2003 | |
|---|---|---|---|
| WO | 95/34563 | 12/1995 | |
| WO | 99/03861 A1 | 1/1999 | |
| WO | 02/48115 A2 | 6/2002 | |
| WO | 02/50071 A1 | 6/2002 | |
| WO | 03/953441 | 3/2003 | ......... A61K 31/4418 |
| WO | 03/091246 | 11/2003 | |
| WO | 2004/014372 A1 | 2/2004 | |
| WO | 2004/054505 A2 | 7/2004 | |
| WO | 2005/007647 A1 | 1/2005 | |

OTHER PUBLICATIONS

Bundgaard:"Design of Prodrugs: Bioreversible derivatives for various functional groups and chemical entities," Elsevier Science Publishers B.V., 1985.

Cesar, et al.:"Trimethylsilyldiazomethane in the Preparation of Diazoketones via Mixed Anhydride and Coupling Reagent Methods: A New Approach to the Arndt-Eistert Synthesis," Tetrahedron Letters, 2001, 42: 7099-7102.

Crosson: Intraocular Pressure Responses to the Adenosine Agonist Cyclohexyladenosine: Evidence for a Dual Mechanism of Action, IOVS, Jul. 2001, 42(8): 1837-1840.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Guillory:"Generation of Polymorphs, Hydrates, Solvates, and Amorphouse Solids," in Polymorphism in Pharmaceutical Solids (Ed. Brittain),1999, pp. 183-226, Marcel Dekker, Inc.

Ibrahim, et al.:"Synthesis and Biological Activity of Some New Heterocyclic Quinoline Derivatives," Phosphorus, Sulfer, and Silicon, 1991, 57: 293-301.

Kambe, et al.:"Synthetic Studies Using $\alpha\beta$-Unsaturated Nitriles: Facile Synthesis of Pyridine Derivatives," Synthesis Communications, Jul. 1981, pp. 531-533.

Quintela, et al.:"Synthesis, Antihistaminic and Cytotoxic Activity of Pyridothieno- and Pyridodithienotriazines", Eur. J. Med. Chem, 1998, 33:887-897.

Ye, et al.:Organic Synthesis with $\alpha$-Diazocarbonyl Compounds, Chem. Rev. 1994, 94:1091-1160.

Sheridan:"The Most Common Chemical Replacements in Drug-Like Compounds," J Chem. Inf. Comput. Sci., 2002, 42:103-108.

Ettmayer, et al.:"Lessons Learned from Marketed and Investigational Prodrugs," J. Med. Chem., May 6, 2004, 47(10) 2393-2404.

Dhalla, et al.:"Pharmacology and Theraputic Applications of A1 Adenosine Receptor Ligands," Current Topics in Medicinal Chemisty, 2003, 3:369-385.

Beaumont, et al.:"Design of Ester Prodrugs to Enhance Oral Absorption of Poorly Permeable Compounds: Challenges to The Discovery Scientist," Current Drug Metabolism, 2003, 4(6):461-485.

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

U.S. Appl. No. 13/2010,889, filed Aug. 16, 2011.

Olah et al., "Cloning, expression, and characterization of the unique bovine A1 adenosine receptor. Studies on the ligand binding site by site-directed mutagenesis," J. Biol. Chem. 267 (1992), 10764-10770.

Klotz et al., "Cloning, expression, and characterization of the unique bovine A1 adenosine receptor. Studies on the ligand binding site by site-directed mutagenesis," J. Biol. Chem. 267 (1992), 10764-10770.

Poulsen et al., "Adenosine receptors: new opportunities for future drugs," Bioorganic and Medicinal Chemistry 6 (1998), 619-641.

* cited by examiner

SUBSTITUTED PHENYLAMINOTHIAZOLES AND USE THEREOF

This application is the U.S. National Stage application under 35 U.S.C. §371 of International Patent Application Serial No. PCT/EP05/09316, filed Aug. 30, 2005, which claims benefit of German Application Serial No. 102004042607.4, filed Sep. 3, 2004, the contents of each of which are incorporated herein by reference in their entirety.

The present application relates to novel phenylaminothiazole derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

Adenosine, a purine nucleoside, is present in all cells and is released by a large number of physiological and pathophysiological stimuli. Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind specifically to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischaemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

The activation of A2b receptors by adenosine or specific A2b agonists leads, via dilation of blood vessels, to a lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis" in *J. Biol. Chem.* 267 (1992), pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: new opportunities for future drugs" in *Bioorganic and Medicinal Chemistry* 6 (1998), pages 619-641]. However, most of these adenosine ligands known from the prior art have the disadvantage that their action is not really receptor-specific, that their activity is less than that of natural adenosine or that they have only very weak activity after oral administration. Thus, they are mainly used only for experimental purposes.

WO 02/06237 discloses aryl-substituted dicyanopyridines as calcium-dependent potassium channel openers and their use for treating disorders of the urogenital tract. Furthermore, WO 01/25210 and WO 02/070485 describe substituted 2-thio-3,5-dicyano-4-aryl-6-aminopyridines as adenosine receptor ligands for treating disorders. WO 03/053441 discloses specifically substituted 2-thio-3,5-dicyano-4-phenyl-6-aminopyridines as selective ligands of the adenosine A1 receptor for treating in particular cardiovascular disorders. WO 02/50071 describes aminothiazole derivatives as tyrosine kinase inhibitors for treating various diseases.

Accordingly, it is an object of the present invention to provide novel compounds which act as selective dual agonists of the adenosine A1 and A2b receptors and which, as such, are suitable for the treatment and/or prevention in particular of hypertension and other cardiovascular disorders.

The present invention provides compounds of the formula (I)

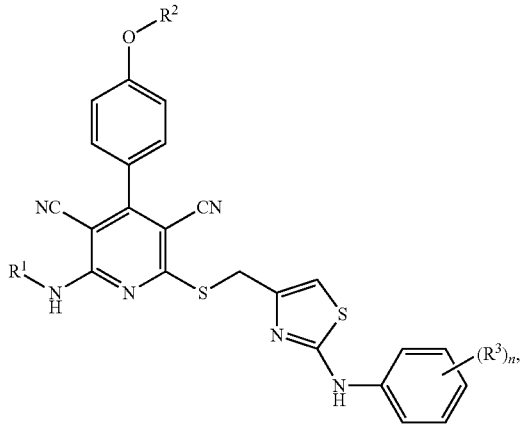

in which
R¹ represents hydrogen or represents $(C_1-C_6)$-alkyl which may be substituted by hydroxyl, amino, mono- or di-$(C_1-C_4)$-alkylamino, pyrrolidino, piperidino, morpholino, piperazino or N'-methylpiperazino,
R² represents $(C_2-C_6)$-alkyl which is mono- or disubstituted by identical or different substituents selected from the group consisting of hydroxyl, $(C_1-C_4)$-alkoxy, amino, mono- and di-$(C_1-C_4)$-alkylamino,
R³ represents a substituent selected from the group consisting of halogen, cyano, nitro, $(C_1-C_6)$-alkyl, hydroxyl, $(C_1-C_6)$-alkoxy, amino, mono- and di-$(C_1-C_6)$-alkylamino, carboxyl and $(C_1-C_6)$-alkoxycarbonyl,
where alkyl and alkoxy for their part may in each case be substituted up to five times by fluorine, and
n represents the number 0, 1, 2, 3, 4 or 5,
where, if the substituent R³ is present more than once, its meanings may be identical or different,
and their salts, solvates and solvates of the salts.

Compounds according to the invention are the compounds of the formula (I) and the salts, solvates and solvates of the salts thereof, the compounds which are encompassed by the formulae (I) and are mentioned in the formulae below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

For the purposes of the invention, $(C_1-C_6)$-alkyl, $(C_2-C_6)$-alkyl, $(C_1-C_4)$-alkyl and $(C_2-C_4)$-alkyl are straight-chain or branched alkyl radicals having 1 to 6, 2 to 6, 1 to 4 and 2 to 4 carbon atoms, respectively. Preference is given to a straight-chain or branched alkyl radical having 1 to 4 or 2 to 4 carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

For the purposes of the invention, $(C_1-C_6)$-alkoxy and $(C_1-C_4)$-alkoxy represent a straight-chain or branched alkoxy radical having 1 to 6 and 1 to 4 carbon atoms, respectively. Preference is given to a straight-chain or branched alkoxy radical having 1 to 4 carbon atoms. The following radicals may be mentioned by way of example and by way of preference: methoxy, ethoxy, n-propoxy, isopropoxy and tert-butoxy.

For the purposes of the invention, $(C_1-C_6)$-alkoxycarbonyl and $(C_1-C_4)$-alkoxycarbonyl represent a straight-chain or branched alkoxy radical having 1 to 6 and 1 to 4 carbon atoms, respectively, which is attached via a carbonyl group. Preference is given to a straight-chain or branched alkoxycarbonyl radical having 1 to 4 carbon atoms in the alkoxy group. The following radicals may be mentioned by way of example and by way of preference: methoxycarbonyl, ethoxycarbonyl, n-propoxycarbonyl, isopropoxycarbonyl and tert-butoxycarbonyl.

For the purposes of the invention, mono-$(C_1-C_6)$-alkylamino and mono-$(C_1-C_4)$-alkylamino represent an amino group having a straight-chain or branched alkyl substituent having 1 to 6 and 1 to 4 carbon atoms, respectively. Preference is given to a straight-chain or branched monoalkylamino radical having 1 to 4 carbon atoms. The following radicals may be mentioned by way of example and by way of preference: methylamino, ethylamino, n-propylamino, isopropylamino and tert-butylamino.

For the purposes of the invention, di-$(C_1-C_6)$-alkylamino and di-$(C_1-C_4)$-alkylamino represent an amino group having two identical or different straight-chain or branched alkyl substituents having in each case 1 to 6 and 1 to 4 carbon atoms, respectively. Preference is given to straight-chain or branched dialkylamino radicals having in each case 1 to 4 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

For the purposes of the invention, halogen includes fluorine, chlorine, bromine and iodine. Preference is given to chlorine or fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three, identical or different substituents. Very particularly preferred is substitution by one or two identical or different substituents.

For the purposes of the present invention, preference is given to compounds of the formula (I)
in which
$R^1$ represents hydrogen or represents $(C_1-C_4)$-alkyl which may be substituted by hydroxyl, amino or dimethylamino,
$R^2$ represents $(C_2-C_4)$-alkyl which is mono- or disubstituted by identical or different substituents selected from the group consisting of hydroxyl, methoxy and amino,
$R^3$ represents a substituent selected from the group consisting of halogen, cyano, nitro, $(C_1-C_4)$-alkyl, hydroxyl, $(C_1-C_4)$-alkoxy, amino, mono- and di-$(C_1-C_4)$-alkylamino, carboxyl and $(C_1-C_4)$-alkoxycarbonyl,
where alkyl and alkoxyl for their part may in each case be substituted up to three times by fluorine, and
n represents the number 0, 1 or 2,
where, if the substituent $R^3$ is present twice, its meanings may be identical or different,
and their salts, solvates and solvates of the salts.

For the purposes of the present invention, particular preference is given to compounds of the formula (I)
in which
$R^1$ represents hydrogen,
$R^2$ represents ethyl, n-propyl or isopropyl which are in each case mono- or disubstituted by identical or different substituents selected from the group consisting of hydroxyl, methoxy and amino,
$R^3$ represents a substituent selected from the group consisting of fluorine, chlorine, bromine, cyano, nitro, methyl, ethyl, trifluoromethyl, hydroxyl, methoxy, ethoxy, amino, mono- and dimethylamino, carboxyl, methoxycarbonyl and ethoxycarbonyl, and
n represents the number 0, 1 or 2,
where, if the substituent $R^3$ is present twice, its meanings may be identical or different,
and their salts, solvates and solvates of the salts.

The present invention furthermore provides a process for preparing the compounds of the formula (I) according to the invention,
characterized in that compounds of the formula (II)

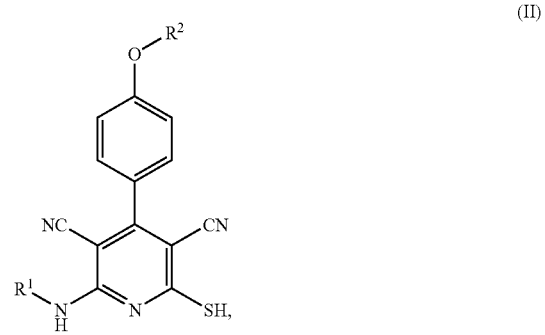

in which $R^1$ and $R^2$ each have the meanings given above,
are reacted in an inert solvent in the presence of base with a compound of the formula (III)

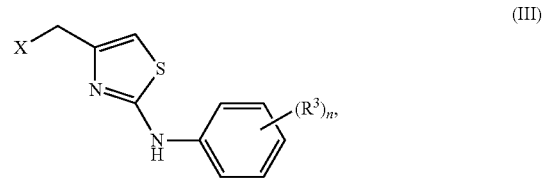

in which $R^3$ and n each have the meanings given above and
X represents a suitable leaving group, preferably halogen, in particular chlorine, bromine or iodine, or mesylate, tosylate or triflate, and the compounds of the formula (I) are, if appropriate, converted into their solvates, salts and/or solvates of the salts using the appropriate (i) solvents and/or (ii) bases or acids.

The process described above can be illustrated in an exemplary manner by the formula scheme below:

Scheme 1

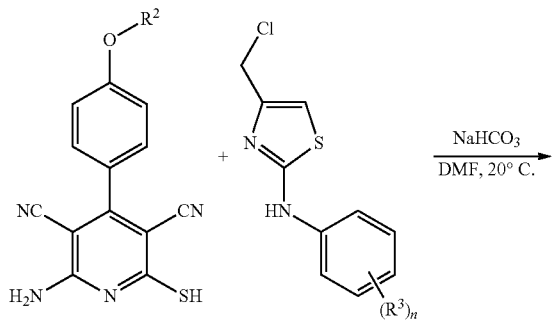

-continued

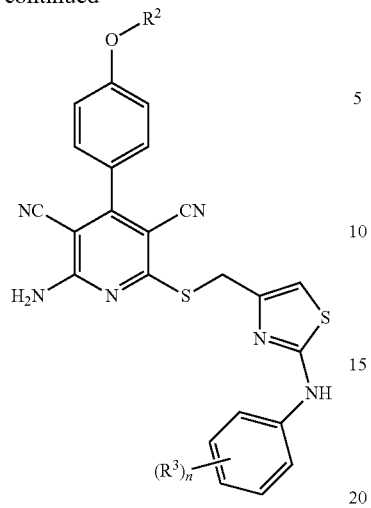

Suitable solvents for the process according to the invention are all organic solvents which are inert under the reaction conditions. These include alcohols, such as methanol, ethanol and isopropanol, ketones, such as acetone and methyl ethyl ketone, acyclic and cyclic ethers, such as diethyl ether, tetrahydrofuran and dioxane, esters, such as ethyl acetate or butyl acetate, hydrocarbons, such as benzene, toluene, xylene, hexane or cyclohexane, chlorinated hydrocarbons, such as dichloromethane or chlorobenzene, or other solvents, such as dimethylformamide, acetonitrile, pyridine or dimethyl sulphoxide. Water is also suitable for use as solvent. It is also possible to use mixtures of the solvents mentioned above. The preferred solvent is dimethylformamide.

Suitable bases are the customary inorganic or organic bases. These preferably include alkali metal hydroxides, such as, for example, sodium hydroxide or potassium hydroxide, alkali metal carbonates, such as sodium carbonate, potassium carbonate or caesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, or amides, such as sodium amide, lithium bis(trimethylsilyl)amide or lithium diisopropylamide, or organometallic compounds, such as butyllithium or phenyllithium, or organic amines, such as triethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (II).

The reaction is generally carried out in a temperature range of from −78° C. to +140° C., preferably in the range from −20° C. to +60° C., in particular at from 0° C. to +40° C. The reaction can be carried out under atmospheric, elevated or reduced pressure (for example in the range from 0.5 to 5 bar). In general, the reaction is carried out under atmospheric pressure.

Compounds of the formula (II) in which $R^1$ represents hydrogen are known per se to the person skilled in the art or can be prepared by customary methods known from the literature. Reference may be made, in particular, to the following publications, the respective contents of which are hereby included by way of reference:

a) Dyachenko et al., *Russian Journal of Chemistry* 33 (7), 1014-1017 (1997) and 34 (4), 557-563 (1998);
b) Dyachenko et al., *Chemistry of Heterocyclic Compounds* 34 (2), 188-194 (1998);
c) Qintela et al., *European Journal of Medicinal Chemistry* 33, 887-897 (1998);
d) Kandeel et al., *Zeitschrift für Naturforschung* 42b, 107-111 (1987).

The compounds of the formula (II) in which $R^1$ represents hydrogen can also be prepared starting with compounds of the formula (IV)

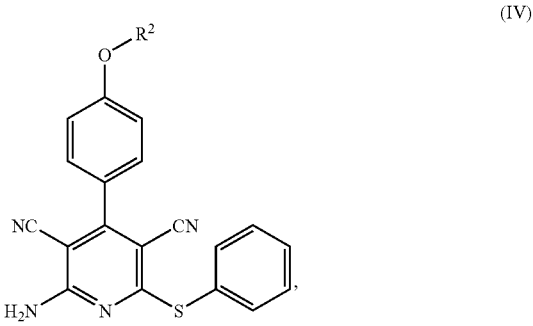

(IV)

in which $R^2$ is as defined above,
by reaction with an alkali metal sulphide. This preparation method can be illustrated in an exemplary manner by the formula scheme below:

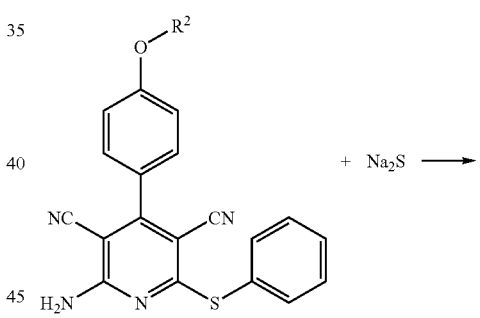

+ Na$_2$S ⟶

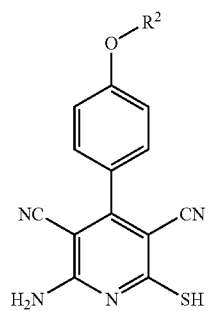

Preferred for use as alkali metal sulphide is sodium sulphide in an amount of from 1 to 10 mol, preferably from 1 to 5 mol, in particular from 1 to 4 mol, based on 1 mol of the compound of the formula (IV).

Suitable solvents are all organic solvents which are inert under the reaction conditions. These preferably include N,N-dimethylformamide, N-methyl-pyrrolidinone, pyridine and acetonitrile. It is also possible to use mixtures of the abovementioned solvents. Particular preference is given to N,N-dimethylformamide.

The reaction is generally carried out in a temperature range of from +20° C. to +140° C., preferably in the range of from +20° C. to +120° C., in particular at from +60° C. to +100° C. The reaction can be carried out under atmospheric, elevated or reduced pressure (for example in the range from 0.5 to 5 bar). In general, the reaction is carried out under atmospheric pressure.

The compounds of the formula (IV) can be prepared analogously to the compounds described in the following publications:
a) Kambe et al., *Synthesis*, 531-533 (1981);
b) Elnagdi et al., *Z. Naturforsch.* 47b, 572-578 (1991).

Compounds of the formula (II) in which $R^1$ does not represent hydrogen can be prepared by initially converting compounds of the formula (IV) with copper(II) chloride and isoamyl nitrite in a suitable solvent into compounds of the formula (V)

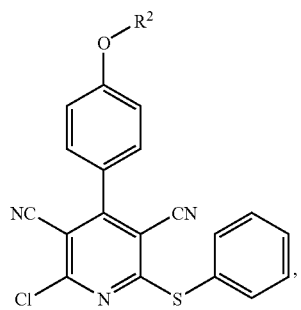

in which $R^2$ is as defined above, then reacting these with a compound of the formula (VI)

$$R^{1A}-NH_2 \qquad (VI),$$

in which $R^{1A}$ has the meaning of $R^1$ given above, but does not represent hydrogen, to give compounds of the formula (VII)

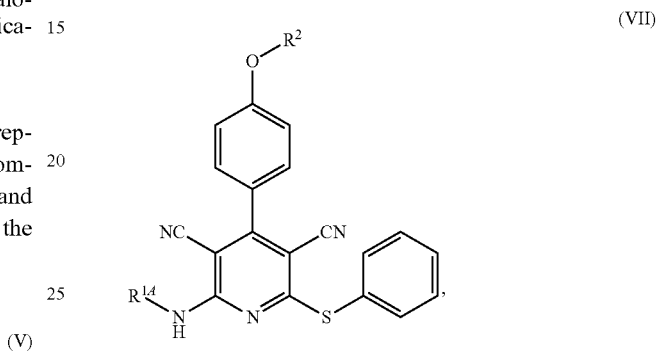

in which $R^{1A}$ and $R^2$ are each as defined above, which are finally converted using sodium sulphide into compounds of the formula (II).

The process described above can be illustrated in an exemplary manner by the formula scheme below:

Scheme 3

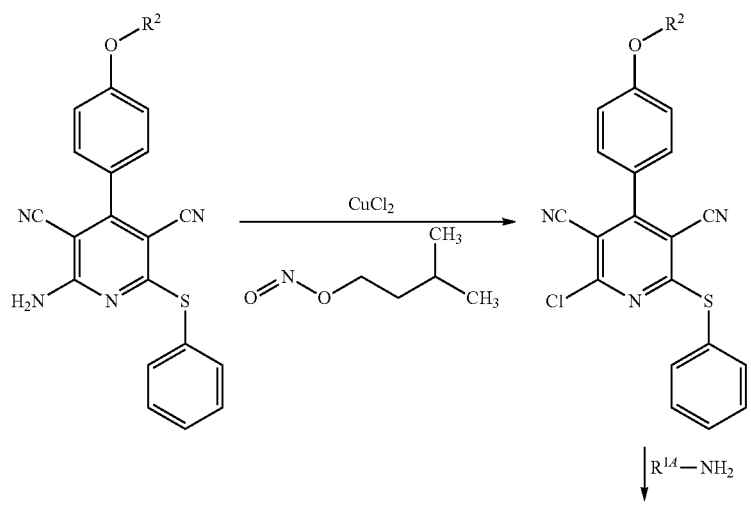

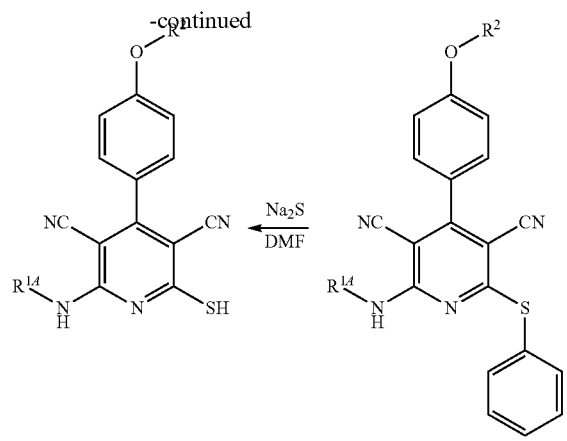

The process step (IV)→(V) is generally carried out using a molar ratio of from 2 to 12 mol of copper(II) chloride and from 2 to 12 mol of isoamyl nitrite per mole of the compound of the formula (IV).

Solvents suitable for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane or cyclohexane, chlorinated hydrocarbons, such as dichloromethane, dichloroethane or chlorobenzene, or other solvents, such as dimethylformamide, acetonitrile or pyridine. It is also possible to use mixtures of the abovementioned solvents. Preferred solvents are acetonitrile and dimethylformamide.

The reaction is generally carried out in a temperature range of from −78° C. to +180° C., preferably in the range of from +20° C. to +100° C., in particular at from +20° C. to +60° C. The reaction can be carried out under atmospheric, elevated or reduced pressure (for example in the range from 0.5 to 5 bar). In general, the reaction is carried out under atmospheric pressure.

The process step (V)+(VI)→(VII) is generally carried out using a molar ratio of from 1 to 8 mol of the compound of the formula (VI) per mole of the compound of the formula (V).

Solvents suitable for this process step are all organic solvents which are inert under the reaction conditions. These include alcohols such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, toluene, xylene, hexane or cyclohexane, chlorinated hydrocarbons, such as dichloromethane, dichloroethane or chlorobenzene, or other solvents, such as dimethylformamide, acetonitrile, pyridine or dimethyl sulphoxide. Another suitable solvent is water. It is also possible to use mixtures of the solvents mentioned above. The preferred solvent is dimethylformamide.

The reaction is generally carried out in a temperature range of from −78° C. to +180° C., preferably in the range of from +20° C. to +160° C., in particular at from +20° C. to +40° C. The reaction can be carried out under atmospheric, elevated or reduced pressure (for example in the range from 0.5 to 5 bar). In general, the reaction is carried out under atmospheric pressure.

The process step (VII)→(II) is generally carried out using a molar ratio of from 1 to 8 mol of sodium sulphide per mole of the compound of the formula (VII).

Solvents suitable for this process step are all organic solvents which are inert under the reaction conditions. These include alcohols such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, toluene, xylene, hexane or cyclohexane, chlorinated hydrocarbons, such as dichloromethane, dichloroethane or chlorobenzene, or other solvents, such as dimethylformamide, acetonitrile, pyridine or dimethyl sulphoxide. It is also possible to use mixtures of the solvents mentioned above. The preferred solvent is dimethylformamide.

The reaction is generally carried out in a temperature range of from −78° C. to +180° C., preferably in the range of from +20° C. to +160° C., in particular at from +40° C. to +100° C. The reaction can be carried out under atmospheric, elevated or reduced pressure (for example in the range from 0.5 to 5 bar). In general, the reaction is carried out under atmospheric pressure.

The compounds of the formula (VI) are either commercially available, known to the person skilled in the art or preparable by customary methods.

Compounds of the formula (III) can be prepared from compounds of the formula (VIII)

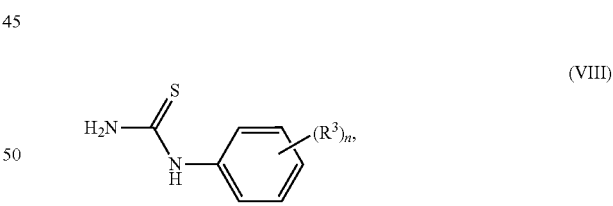

in which $R^3$ and n are as defined above, by reaction with a 1,3-dihaloacetone. This preparation method can be illustrated in an exemplary manner by the formula scheme below:

Scheme 4

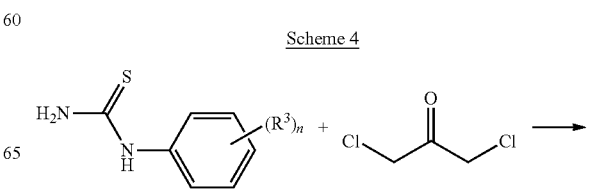

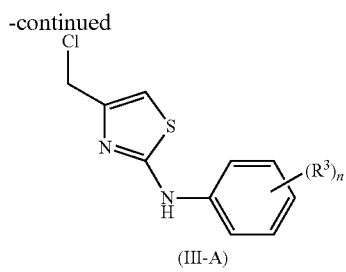

(III-A)

Here, the compounds of the formula (III-A) can either be prepared and isolated analogously to the literature [I. Simiti et al., *Chem. Ber.* 95, 2672-2679 (1962)], or they can be generated in situ and directly reacted further with a compound of the formula (II). Preference is given to the in situ generation from 1,3-dichloroacetone and a compound of the formula (VIII) in dimethylformamide or ethanol. The preparation is generally carried out in a temperature range of from 0° C. to +140° C., preferably in the range of from +20° C. to +120° C., in particular at from +80° C. to +100° C.

The compounds of the formula (VIII) are either commercially available, known to the person skilled in the art or preparable by customary methods.

Surprisingly, the compounds according to the invention have an unforeseeable useful pharmacological activity spectrum and are therefore suitable in particular for the prophylaxis and/or treatment of disorders.

The pharmaceutical activity of the compounds according to the invention can be explained by their action as selective ligands on adenosine A1 and A2b receptors. Here, they act as dual A1/A2b agonists.

In the context of the present invention, "selective ligands on adenosine A1 and A2b receptors" are adenosine receptor ligands where on the one hand a clear activity can be observed on A1 and A2b adenosine receptor subtypes and on the other hand no or a considerably weaker activity (by a factor 10 or higher) can be observed on A2a and A3 adenosine receptor subtypes, where, for the test methods for the selectivity of action, reference is made to the tests described in Section B-1.

The compounds of the formula (I), alone or in combination with one or more other active compounds, are suitable for the prophylaxis and/or treatment of various disorders, i.e. in particular, for example, hypertension and other disorders of the cardiovascular system (cardiovascular disorders). Active compounds suitable for combinations are in particular active compounds for treating hypertension and/or coronary heart diseases, such as beta blockers, calcium antagonists, diuretics, ACE inhibitors, AT1 antagonists and nitrates.

In the context of the present invention, cardiovascular disorders are to be understood as meaning, in particular, for example the following disorders besides hypertension: coronary restenosis, such as, for example, restenosis after balloon dilation of peripheral blood vessels, tachycardia, arrhythmias, peripheral vascular disorders and cardiovascular disorders, stable and unstable angina pectoris, atrial and ventricular fibrillation and myocardial insufficiency.

The compounds of the formula (I) are furthermore also particularly suitable, for example, for reducing the size of myocardial area affected by an infarct and for the prophylaxis of secondary infarcts.

Furthermore, the compounds of the formula (I) are particularly suitable, for example, for the prophylaxis and/or treatment of thromboembolic disorders and ischaemias, such as myocardial infarction, stroke and transitory ischaemic attacks.

Further areas of indication for which the compounds of the formula (I) are particularly suitable are, for example, the prophylaxis and/or treatment of disorders of the urogenital region, such as, for example, irritable bladder, erectile dysfunction and female sexual dysfunction, and additionally also the prophylaxis and/or treatment of inflammatory disorders, such as, for example, asthma and inflammable dermatoses, of neuroinflammatory disorders of the central nervous system, such as, for example, conditions after cerebral infarction, Alzheimer's disease, furthermore also of neurodegenerative disorders, as well as of pain, cancer and nausea and vomiting associated with cancer therapies.

A further particular area of indication is, for example, the prophylaxis and/or treatment of disorders of the respiratory tract, such as, for example, asthma, chronic bronchitis, pulmonary emphysema, bronchiectases, cystic fibrosis (mucoviscidosis) and pulmonary hypertension.

Finally, the compounds of the formula (I) are in particular also suitable, for example, for the prophylaxis and/or treatment of diabetes, in particular diabetes mellitus, of the metabolic syndrome and of dyslipidaemias.

The present invention also relates to the use of the compounds of the formula (I) for preparing medicaments for the prophylaxis and/or treatment of the clinical pictures mentioned above.

The present invention furthermore relates to a method for the prophylaxis and/or treatment of the clinical pictures mentioned above using the compounds of the formula (I).

The subject-matter of the present invention furthermore includes medicaments comprising at least one compound according to the invention, usually together with one or more inert, nontoxic, pharmaceutically suitable auxiliaries, and their use for the purposes mentioned above.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or optic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilizates or sterile powders.

Examples suitable for other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, (e.g. patches), milk, pastes, foams, dusting powders, implants or stents.

Preference is given to oral or parenteral administration, in particular oral administration.

The compounds according to the invention can be converted into the stated administration forms. This can take place in a manner known per se by mixing with inert, non-toxic, pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

In general, it has proved advantageous to administer on parenteral administration amounts of from about 0.001 to 1 mg/kg, preferably from about 0.01 to 0.5 mg/kg, of body weight to achieve effective results. The dosage on oral administration is from about 0.01 to 100 mg/kg, preferably about 0.01 to 20 mg/kg, and very particularly preferably 0.1 to 10 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The invention is illustrated by the working examples below. The invention is not limited to the examples.

The percentage data in the following tests and examples are percentages by weight unless otherwise indicated; parts are parts by weight. Solvent ratios, dilution ratios and concentration data of liquid/liquid solutions are in each case based on volume.

A. Examples

Abbreviations Used
Ex. Example
TLC thin-layer chromatography
DCI direct chemical ionization (in MS)
DMF N,N-dimethylformamide
DMSO dimethyl sulphoxide
EA ethyl acetate
EI electron impact ionization (in MS)
ESI electrospray ionization (in MS)
m.p. melting point
sat. saturated
h hour(s)
HPLC high-pressure, high-performance liquid chromatography
conc. concentrated
LC-MS liquid chromatography-coupled mass spectroscopy
LDA lithium diisopropylamide
Lit. literature (reference)
sol. solution
min minute(s)
MS mass spectroscopy
NMR nuclear magnetic resonance spectroscopy
RP-HPLC reverse phase HPLC
RT room temperature
$R_t$ retention time (in HPLC)
THF tetrahydrofuran
dil. diluted
aq. aqueous
HPLC- and LC-MS methods:
Method 1 (HPLC):
Instrument: Hewlett Packard Series 1050; column: Symmetry TM C18 3.9×150 mm; flow rate: 1.5 ml/min; mobile phase A: water, mobile phase B: acetonitrile; gradient: →0.6 min 10% B→3.8 min 100% B→5.0 min 100% B→5.5 min 10% B; stop time: 6.0 min; injection volume: 10 µl; diode array detector signal: 214 and 254 nm.
Method 2 (LC-MS):
Instrument: Micromass Quattro LCZ with HPLC Agilent Series 1100; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.
Method 3 (LC-MS):
MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 4 (LC-MS):
MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (LC-MS):

MS instrument type: Micromass ZQ; HPLC instrument type: Waters Alliance 2795; column: Merck Chromolith SpeedROD RP-18e 100 mm×4.6 mm; mobile phase A: water+500 µl of 50% strength formic acid/l, mobile phase B: acetonitrile+500 µl of 50% strength formic acid/l; gradient: 0.0 min 10% B→7.0 min 95% B→9.0 min 95% B; oven: 35° C.; flow rate: 0.0 min 1.0 ml/min ~7.0 min 2.0 ml/min→9.0 min 2.0 ml/min; UV detection: 210 nm.

Method 6 (HPLC):

Instrument: HP 1100 with DAD detection; column: Kromasil RP-18, 60 mm×2 mm, 3.5 µm; mobile phase A: 5 ml of $HClO_4$/l of water, mobile phase B: acetonitrile; gradient: 0 min 2% B→0.5 min 2% B→4.5 min 90% B→9 min 90% B; flow rate: 0.75 ml/min; oven: 30° C.; UV detection: 210 nm.

Method 7 (HPLC):

Instrument: HP 1100 with DAD detection; column: Kromasil RP-18, 60 mm×2 mm, 3.5 µm; mobile phase A: 5 ml of $HClO_4$/l of water, mobile phase B: acetonitrile; gradient: 0 min 2% B→0.5 min 2% B→4.5 min 90% B→6.5 min 90% B; flow rate: 0.75 ml/min; oven: 30° C.; UV detection: 210 nm.

Starting Materials and Intermediates:

Example 1A

4-[(2,2-Dimethyl-1,3-dioxolan-4-yl)methoxy]benzaldehyde

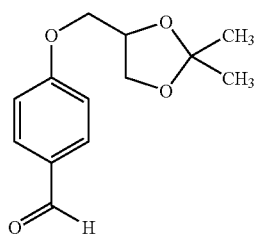 [SMILES: CC1(C)OCC(COc2ccc(C=O)cc2)O1]

39.3 g (150 mmol) of triphenylphosphine are added to a solution of 13.2 g (100 mmol) of 1,2-O-isopropylideneglycerol in 250 ml of dry THF, and the mixture is stirred at RT for 30 min. The mixture is cooled to about 0° C., and 12.2 g (100 mmol) of 4-hydroxybenzaldehyde and 31.9 g (150 mmol) of diisopropyl azodicarboxylate (DIAD) are added. The yellow reaction solution is stirred at RT for 16 h. The mixture is then concentrated using a rotary evaporator, and the residue is added to 150 ml of sat. sodium bicarbonate solution. The mixture is extracted with ethyl acetate (three times, 150 ml each), and the combined organic phases are dried over sodium sulphate. After removal of the solvent on a rotary evaporator, the crude product is purified chromatographically on silica gel 60 (mobile phase gradient cyclohexane→cyclohexane/ethyl acetate 2:1).

Yield: 5.03 g (21% of theory)

LC-MS (Method 3): $R_t$=1.86 min; MS (ESIpos): m/z=237 $[M+H]^+$.

Example 2A

{4-[(2,2-Dimethyl-1,3-dioxolan-4-yl)methoxy]benzylidene}malononitrile

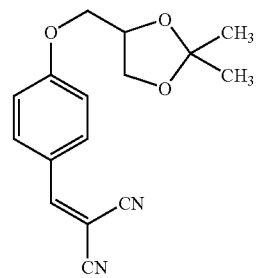 [SMILES: CC1(C)OCC(COc2ccc(C=C(C#N)C#N)cc2)O1]

0.13 g (1.98 mmol) of malononitrile, 0.45 g (1.90 mmol) of the compound from Example 1A and 5.7 µl (0.06 mmol) of piperidine are dissolved in ethanol, and the mixture is heated under reflux for 3.5 h. The reaction solution is concentrated and the residue is purified chromatographically on silica gel 60 (mobile phase gradient cyclohexane→cyclohexane/ethyl acetate 2:1).

Yield: 0.43 g (79% of theory)

$^1$H-NMR (400 MHz, $CDCl_3$): δ=7.91 (d, 2H), 7.65 (s, 1H), 7.03 (d, 2H), 4.51 (m, 1H) 4.19 (dd, 1H), 4.14 (dd, 1H), 4.06 (dd, 1H), 3.91 (dd, 1H), 1.46 (s, 3H), 1.41 (s, 3H).

MS (DCI, $NH_3$): m/z=302 $[M+NH_4]^+$.

Example 3A

2-Amino-4-{4-[(2,2-dimethyl-1,3-dioxolan-4-yl)methoxy]phenyl}-6-mercaptopyridine-3,5-dicarbonitrile

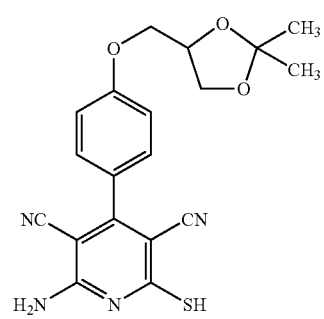

0.43 g (1.51 mmol) of the compound from Example 2A, 0.38 g (3.78 mmol) of cyanothioacetamide and 0.38 g (3.78 mmol) of 4-methylmorpholine are dissolved in 15 ml of ethanol, and the mixture is stirred under reflux for 6 h. After cooling, the reaction solution is concentrated using a rotary evaporator, and the residue is chromatographed on silica gel 60. After removal of by-products (mobile phase gradient cyclohexane→cyclohexane/ethyl acetate 1:1), the product fractions are eluted (mobile phase gradient ethyl acetate→ethyl acetate/methanol 20:1). This is followed by fine purification via preparative HPLC (column: YMC GEL ODS-AQ S-5/15 µm; mobile phase gradient: acetonitrile/water 10:90→95:5).

Yield: 88 mg (15% of theory)

¹H-NMR (400 MHz, DMSO-d₆): δ=12.96 (br. s, 1H), 7.90 (br. s, 2H), 7.46 (d, 2H), 7.12 (d, 2H), 4.44 (m, 1H), 4.18-4.02 (m, 3H), 3.79 (m, 1H), 1.37 (s, 3H), 1.32 (s, 3H).

LC-MS (Method 3): $R_t$=1.76 min; MS (ESIpos): m/z=383 [M+H]⁺.

Example 4A

4-[(4-{[(6-Amino-3,5-dicyano-4-{4-[(2,2-dimethyl-1,3-dioxolan-4-yl)methoxy]phenyl}pyridin-2-yl)thio]methyl}-1,3-thiazol-2-yl)amino]benzoic acid

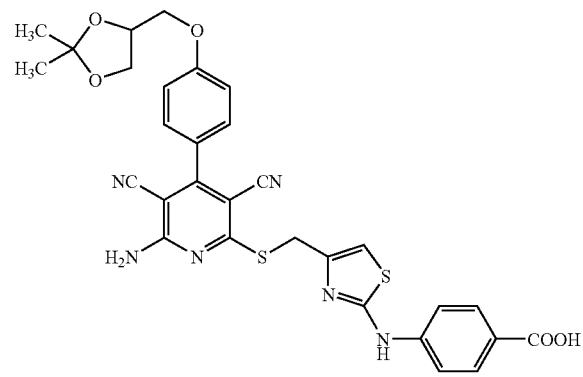

177 mg (0.90 mmol) of 4-carboxyphenylthiourea and 111 mg (0.87 mmol) of 1,3-dichloroacetone are dissolved in 3 ml of DMF, and the reaction solution is stirred at 100° C. for 60 min. After cooling, 230 mg (0.60 mmol) of the compound from Example 3A and 151 mg (1.80 mmol) of sodium bicarbonate are added, and the mixture is stirred at RT for a further 16 h. The reaction mixture is purified directly by preparative HPLC chromatography (column: YMC GEL ODS-AQ S-5/15 µm; mobile phase gradient: acetonitrile/water 10:90→95:5).

Yield: 134 mg (36% of theory)

¹H-NMR (400 MHz, CDCl₃): δ=12.5 (m, 1H), 10.6 (s, 1H), 8.07 (br. s, 2H), 7.86 (d, 2H), 7.67 (d, 2H), 7.49 (d, 2H), 7.12 (d, 2H), 7.07 (s, 1H), 4.50 (s, 2H), 4.44 (m, 1H), 4.16-4.03 (m, 3H), 3.78 (dd, 1H), 1.37 (s, 3H), 1.31 (s, 3H).

LC-MS (Method 4): $R_t$=2.51 min; MS (ESIpos): m/z=615 [M+H]⁺.

Example 5A

2-Amino-4-{4-[(2,2-dimethyl-1,3-dioxolan-4-yl)methoxy]phenyl}-6-[({2-[(4-fluorophenyl)amino]-1,3-thiazol-4-yl}methyl)thio]pyridine-3,5-dicarbonitrile

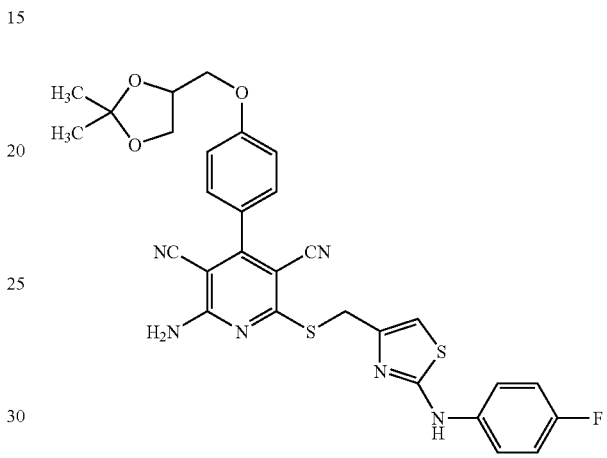

102 mg (0.6 mmol) of 4-fluorophenylthiourea and 73.6 mg (0.58 mmol) of 1,3-dichloroacetone are dissolved in 2.5 ml of ethanol, and the mixture is stirred under reflux for 60 min. The mixture is allowed to cool and concentrated using a rotary evaporator. The residue is taken up in 1.5 ml of DMF, 153 mg (0.4 mmol) of the compound from Example 3A and 101 mg (1.2 mmol) of sodium bicarbonate are added and the reaction solution is stirred at RT for a further 16 h. The reaction mixture is purified directly by preparative HPLC chromatography (column: YMC GEL ODS-AQ S-5/15 µm; mobile phase gradient: acetonitrile/water 10:90→95:5).

Yield: 62 mg (26% of theory)

¹H-NMR (400 MHz, DMSO-d₆): δ=10.24 (s, 1H), 8.08 (br. s, 2H), 7.62 (dd, 2H), 7.47 (d, 2H), 7.13 (m, 4H), 6.97 (s, 1H), 4.49-4.39 (m, 3H), 4.10 (m, 3H), 3.78 (dd, 1H), 1.36 (s, 3H), 1.31 (s, 3H).

LC-MS (Method 2): $R_t$=2.51 min; MS (ESIpos): m/z=589 [M+H]⁺.

The examples listed in Table 1 are prepared from the corresponding starting materials, analogously to Example 5A:

TABLE 1
| Example No. | Structure | MS (ESI) [M + H]+ | LC-MS R_t [min] (Method) | Yield (% of theory) |
|---|---|---|---|---|
| 6A | 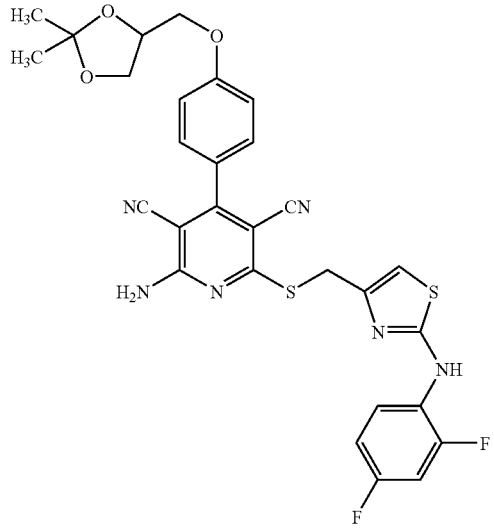 | 607 | 2.62 (3) | 39 |
| 7A | 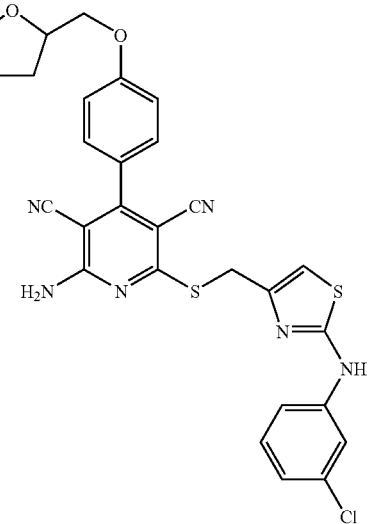 | 605 | 2.96 (4) | 53 |

TABLE 1-continued
| Example No. | Structure | MS (ESI) [M + H]+ | LC-MS Rt [min] (Method) | Yield (% of theory) |
|---|---|---|---|---|
| 8A | 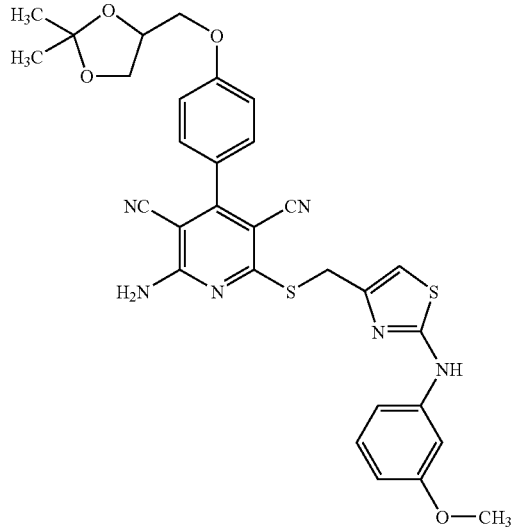 | 601 | 2.80 (4) | 40 |
| 9A | 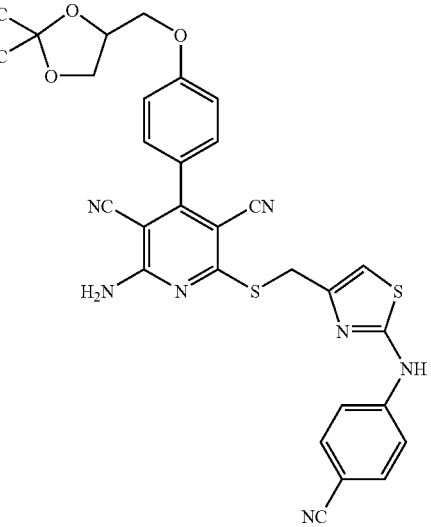 | 596 | 2.74 (4) | 38 |

TABLE 1-continued

| Example No. | Structure | MS (ESI) [M + H]+ | LC-MS R_t [min] (Method) | Yield (% of theory) |
|---|---|---|---|---|
| 10A | 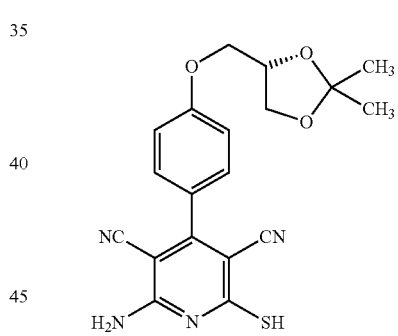 | 585 | 2.89 (4) | 46 |

Example 11A (S)-4-[(2,2-Dimethyl-1,3-dioxolan-4-yl)methoxy]benzaldehyde

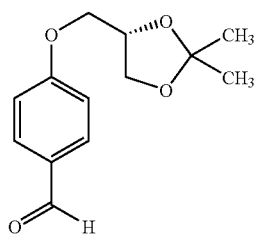 [SMILES: CC1(C)OC[C@H](COc2ccc(C=O)cc2)O1]

1.79 g (14.6 mmol) of p-hydroxybenzaldehyde are dissolved in absolute DMF (10 ml), and 14.2 g (102.5 mmol) of potassium carbonate and 3.3 g (22.0 mmol) of (R)-(+)-4-chloromethyl-2,2-dimethyl-1,3-dioxolane are added. The mixture is heated at 150° C. for 24 h. The mixture is then concentrated using a rotary evaporator, and the residue is ispartitioned between dichloromethane and water. The combined organic phases are extracted with dichloromethane (three times, 20 ml each), washed with sat. sodium chloride solution and dried over magnesium sulphate. After removal of the solvent on a rotary evaporator, the crude product is purified chromatographically on silica gel 60 (mobile phase: cyclohexane/ethyl acetate 5:1).

Yield: 2.12 g (61% of theory)

LC-MS (Method 2): $R_t$=1.97 min; MS (ESIpos): m/z=237 [M+H]+.

Example 12A (S)-2-Amino-4-{4-[(2,2-dimethyl-1,3-dioxolan-4-yl)methoxy]phenyl}-6-mercaptopyridine-3,5-dicarbonitrile 1.52 g (6.43 mmol) of the compound from Example 11A, 1.29 g (12.9 mmol) of cyanothioacetamide and 1.3 g (12.9 mmol) of 4-methylmorpholine are dissolved in 15 ml of ethanol, and the mixture is stirred under reflux for 3 h. The mixture is then stirred at RT for 18 h. The reaction solution is concentrated using a rotary evaporator, and the residue is chromatographed on silica gel 60 (mobile phase: dichloromethane/ethanol 10:1).

Yield: 1.06 g (43% of theory)

LC-MS (Method 3): $R_t$=1.75 min; MS (ESIpos): m/z=383 [M+H]+.

Example 13A (S)-2-Amino-4-{4-[(2,2-dimethyl-1,3-dioxolan-4-yl)methoxy]phenyl}-6-[({2-[(4-fluorophenyl)-amino]-1,3-thiazol-4-yl}methyl)thio]pyridine-3,5-dicarbonitrile

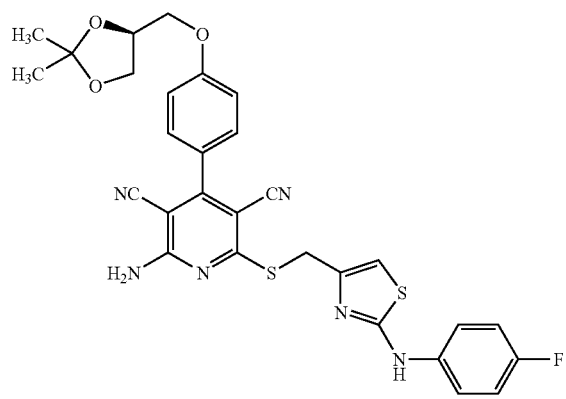

The synthesis is carried out analogously to Example 5A using the enantiomerically pure starting material from Example 12A.

Yield: 47% of theory

LC-MS (Method 3): $R_t$=2.58 min; MS (ESIpos): m/z=589 $[M+H]^+$.

The examples listed in Table 2 are prepared from the corresponding starting materials analogously to Example 5A or 13A or the corresponding enantiomer:

TABLE 2

| Example No. | Structure | MS (ESI) $[M + H]^+$ | LC-MS $R_t$ [min] (Method) | Yield (% of theory) |
|---|---|---|---|---|
| 14A | 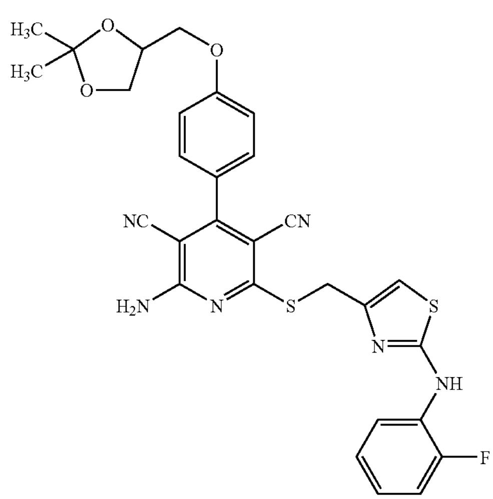 | 589 | 2.77 (2) | 50 |

TABLE 2-continued

| Example No. | Structure | MS (ESI) [M + H]+ | LC-MS Rt [min] (Method) | Yield (% of theory) |
|---|---|---|---|---|
| 15A | 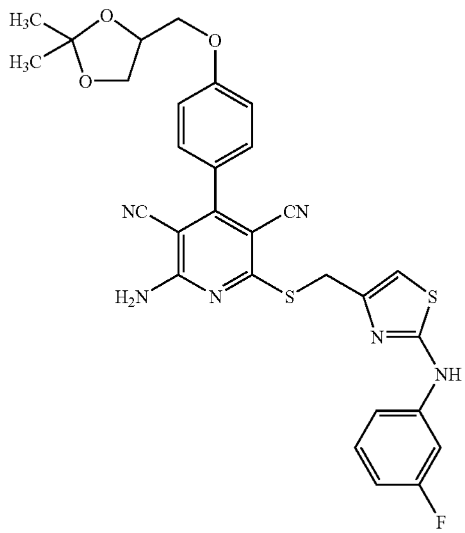 | 589 | 2.60 (3) | 36 |
| 16A | 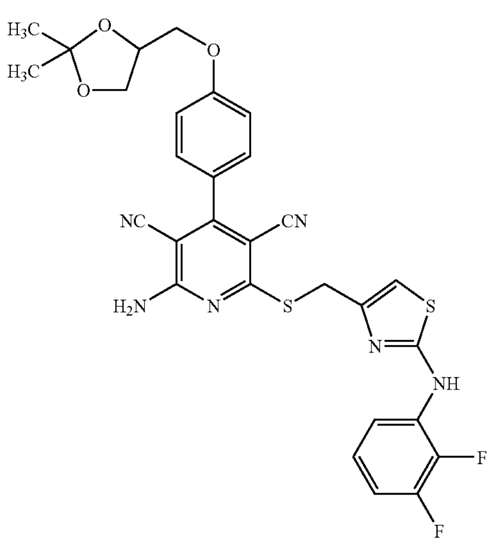 | 607 | 2.64 (3) | 52 |

TABLE 2-continued

| Example No. | Structure | MS (ESI) [M + H]+ | LC-MS R_t [min] (Method) | Yield (% of theory) |
|---|---|---|---|---|
| 17A | 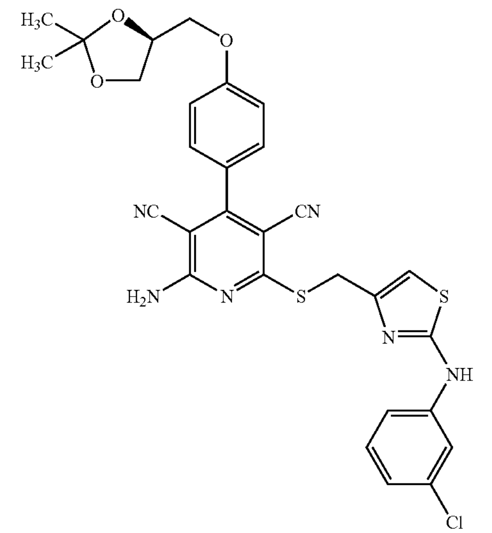 | 605 | 2.71 (3) | 33 |
| 18A | 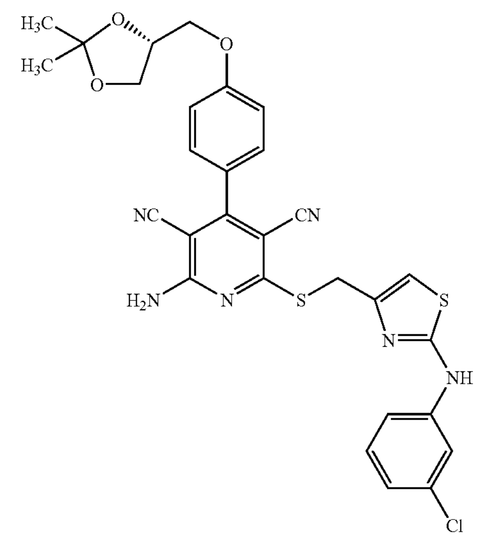 | 605 | 2.71 (3) | 54 |
| 19A | 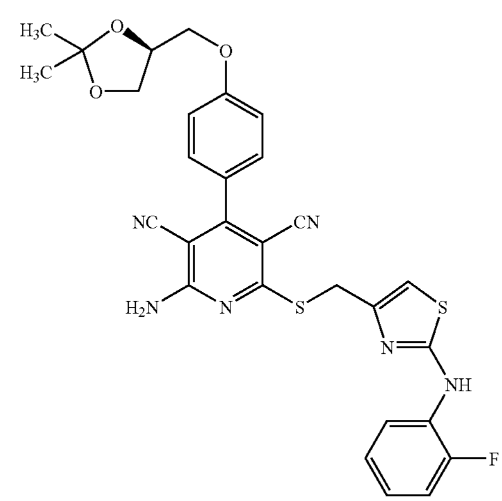 | 589 | 2.76 (2) | 61 |

TABLE 2-continued
| Example No. | Structure | MS (ESI) [M + H]+ | LC-MS Rt [min] (Method) | Yield (% of theory) |
|---|---|---|---|---|
| 20A | 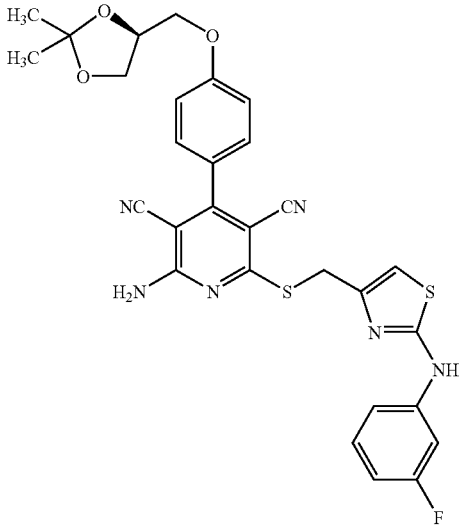 | 589 | 2.60 (3) | 18 |
| 21A | 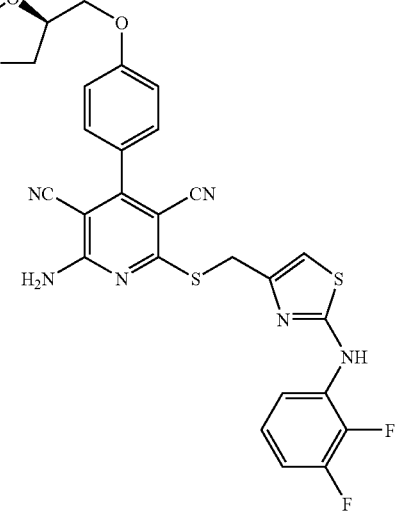 | 607 | 2.87 (4) | 41 |

TABLE 2-continued
| Example No. | Structure | MS (ESI) [M + H]+ | LC-MS Rt [min] (Method) | Yield (% of theory) |
|---|---|---|---|---|
| 22A | 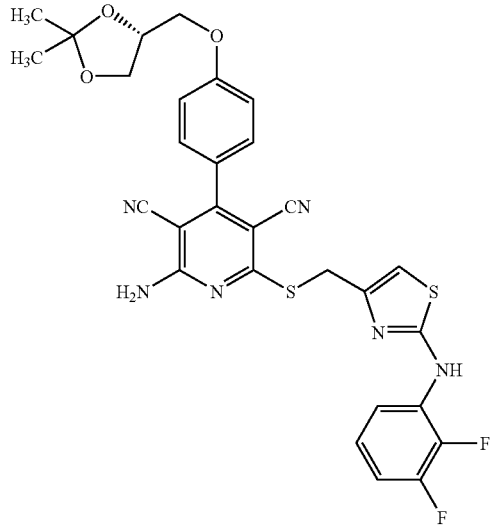 | 607 | 2.83 (2) | 23 |
| 23A | 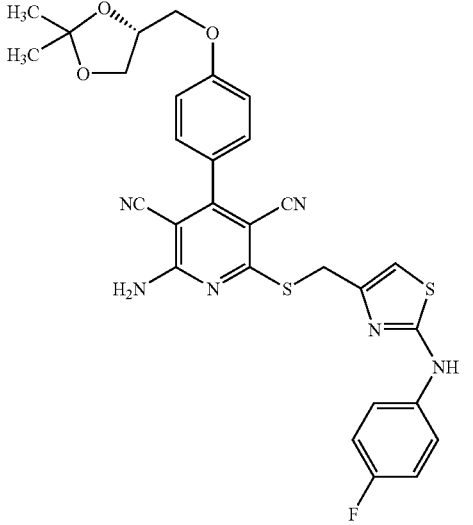 | 589 | 2.58 (3) | 80 |

TABLE 2-continued
| Example No. | Structure | MS (ESI) [M + H]+ | LC-MS R_t [min] (Method) | Yield (% of theory) |
|---|---|---|---|---|
| 24A | 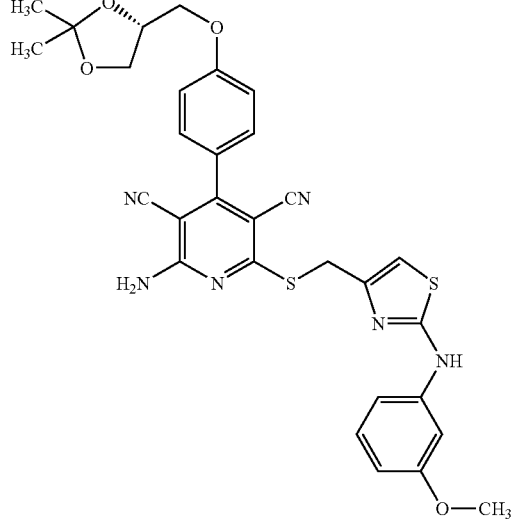 | 601 | 2.88 (4) | 67 |
| 25A | 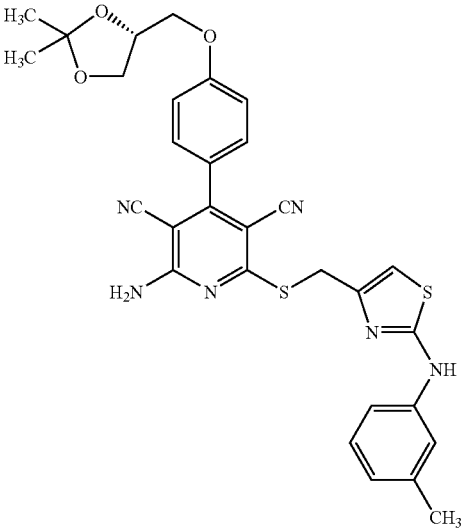 | 585 | 3.01 (4) | 62 |

TABLE 2-continued

| Example No. | Structure | MS (ESI) [M + H]+ | LC-MS Rt [min] (Method) | Yield (% of theory) |
|---|---|---|---|---|
| 26A | 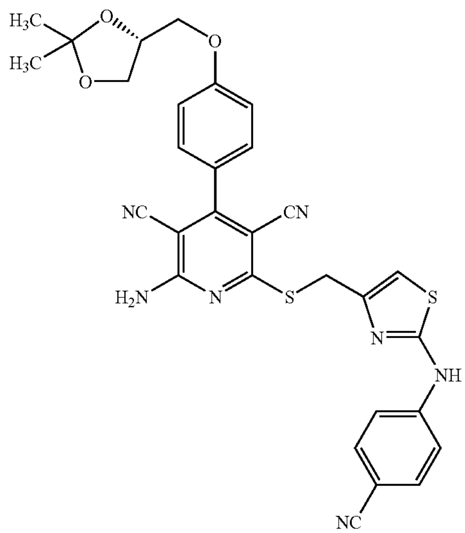 | 596 | 2.84 (4) | 45 |
| 27A | 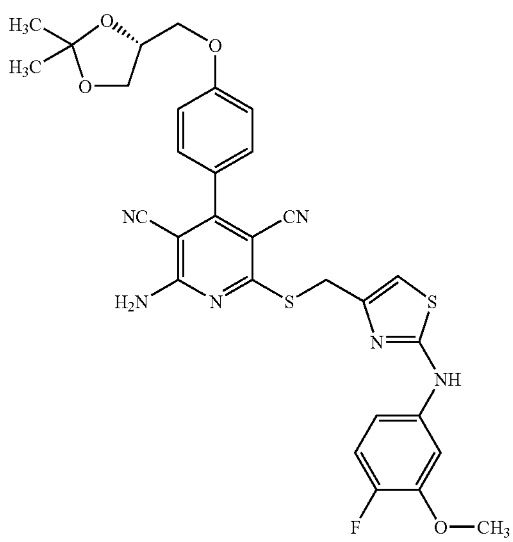 | 619 | 2.79 (4) | 68 |
| 28A | 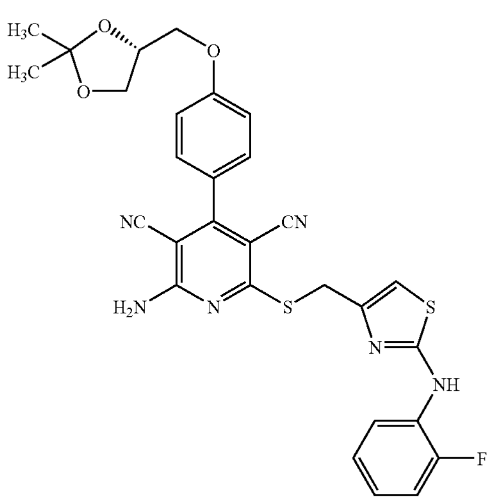 | 589 | 2.80 (4) | 66 |

Example 29A

2-Amino-4-[4-(2-hydroxyethoxy)phenyl]-6-phenylthiopyridine-3,5-dicarbonitrile

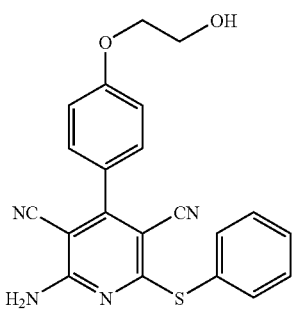

0.765 g (11.6 mmol) of malononitrile, 1.28 g (11.6 mmol) of thiophenol and 2.48 g (11.6 mmol) of 2-[4-(2-hydroxyethoxy)benzylidene]malononitrile [preparation according to WO 03/053441, Example 6/Method 2, Step 1] are dissolved in 15 ml of ethanol, and 0.03 ml of triethylamine is added. The mixture is stirred under reflux for 2 h. After cooling, the reaction mixture is filtered and the residue is washed with ethanol and dried.

Yield: 2.07 g (46% of theory)

$^1$H-NMR (400 MHz, DMSO-$d_6$): δ=7.76 (br. s, 2H), 7.60 (m, 2H), 7.51 (m, 5H), 7.12 (d, 2H), 4.93 (t, 1H), 4.09 (t, 2H), 3.75 (m, 2H).

LC-MS (Method 3): $R_t$=2.02 min; MS (ESIpos): m/z=389 [M+H]$^+$.

Example 30A

2-Chloro-4-[4-(2-hydroxyethoxy)phenyl]-6-phenylthiopyridine-3,5-dicarbonitrile

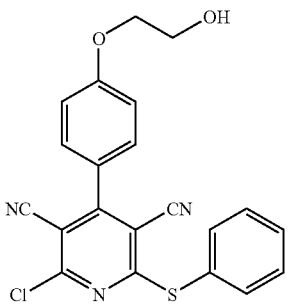

2.07 g (5.33 mmol) of the compound from Example 29A are dissolved in 11 ml of absolute DMF, and 4.30 g (32.0 mmol) of anhydrous copper(II) chloride and 2.71 ml (32.0 mmol) of isoamyl nitrite are added. The mixture is stirred at 40° C. for 18 h. The reaction solution is then concentrated using a rotary evaporator, and the residue is added to 1N hydrochloric acid. The mixture is extracted three times with dichloromethane, and the combined organic phases are washed with 1N hydrochloric acid and sodium chloride solution. After drying over magnesium sulphate, the solvent is removed on a rotary evaporator. The crude product is purified chromatographically on silica gel 60 (mobile phase: dichloromethane/ethanol 20:1).

Yield: 1.29 g (59% of theory)

$^1$H-NMR (400 MHz, DMSO-$d_6$): δ=7.60 (m, 7H), 7.20 (d, 2H), 4.12 (t, 2H), 3.76 (t, 2H).

LC-MS (Method 3): $R_t$=2.38 min; MS (ESIpos): m/z=408 [M+H]$^+$.

Example 31A 2-(2-Hydroxyethoxy)amino-4-[4-(2-hydroxyethoxy)phenyl]-6-phenylthiopyridine-3,5-dicarbonitrile

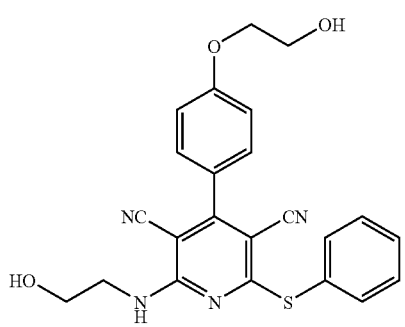

0.50 g (1.23 mmol) of the compound from Example 30A is dissolved in 1.5 ml of DMF, and 0.16 ml (2.70 mmol) of 2-hydroxyethylamine is added. The mixture is stirred for 20 min, and 2 ml of methanol and 4 ml of water are then added. The precipitate is filtered off, washed with methanol and dried.

Yield: 0.36 g (68% of theory)

$^1$H-NMR (400 MHz, DMSO-$d_6$): δ=7.94 (br. s, 1H), 7.55 (m, 7H), 7.13 (d, 2H), 4.93 (t, 1H), 4.49 (t, 1H), 4.09 (t, 2H), 3.75 (m, 2H), 3.09 (m, 2H), 3.00 (m, 2H).

LC-MS (Method 4): $R_t$=2.33 min; MS (ESIpos): m/z=433 [M+H]$^+$.

Example 32A 2-(2-Hydroxyethoxy)amino-4-[4-(2-hydroxyethoxy)phenyl]-6-mercaptopyridine-3,5-dicarbonitrile

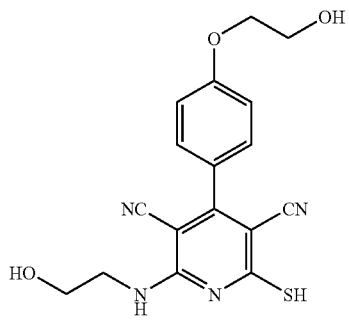

0.30 g (0.70 mmol) of the compound from Example 31A is dissolved in 2 ml of DMF, and 0.19 g (2.43 mmol) of sodium sulphide is added. The mixture is stirred at 80° C. for 2 h and then at RT for 12 h. 1N hydrochloric acid (10 ml) is then added, and the precipitate is filtered off.

Yield: 0.25 g (72% of theory)

LC-MS (Method 3): $R_t$=1.21 min; MS (ESIpos): m/z=357 [M+H]$^+$.

Example 33A

2-Amino-6-(benzylthio)-4-{4-[2-(dimethylamino)ethoxy]phenyl}pyridine-3,5-dicarbonitrile

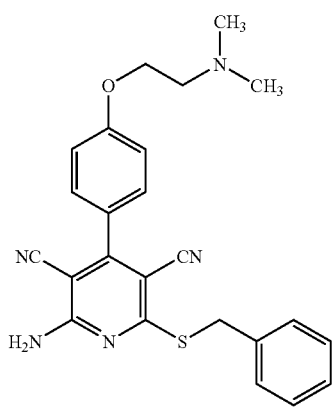

6.31 g (56.2 mmol) of potassium tert-butoxide are added to a solution of 8.39 g (23.4 mmol) of 2-amino-6-(benzylthio)-4-(4-hydroxyphenyl)pyridine-3,5-dicarbonitrile [preparation according to WO 01/25210, Example A 383, from 2-amino-4-(4-hydroxyphenyl)-6-mercaptopyridine-3,5-dicarbonitrile and benzyl bromide] in 105.5 ml of ethanol. The mixture is stirred at RT for 1 h, and 4.05 g (28.1 mmol) of 2-dimethylaminoethyl chloride hydrochloride are then added. The mixture is then stirred at +78° C. for 3 h. After cooling, the reaction mixture is filtered and the filtrate is concentrated using a rotary evaporator. The residue is purified directly by preparative HPLC (column: Merck 210 g RP silica gel Gromsil 120ODS-4 HR 10 μm, 50 mm×200 mm; mobile phase A=water+0.1% formic acid, mobile phase B=acetonitrile; gradient: 0 min 10% B→5 min 10% B→6 min 90% B→22 min 90% B→22 min 10% B→28 min 10% B; flow rate: 110 ml/min; wavelength: 220 nm).

Yield: 3.55 g (35% of theory)

LC-MS (Method 3): $R_t$=1.57 min; MS (ESIpos): m/z=430 [M+H]$^+$.

Example 34A

2-Amino-4-{4-[2-(dimethylamino)ethoxy]phenyl}-6-mercaptopyridine-3,5-dicarbonitrile

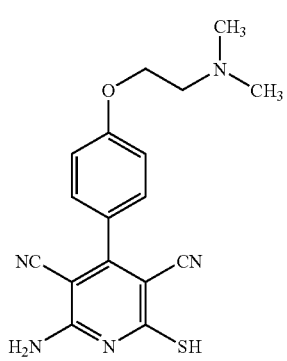

0.97 g (12.41 mmol) of sodium sulphide is added to a solution of 3.56 g (8.28 mmol) of the compound from Example 33A in 13 ml of dry DMF. The reaction mixture is stirred at +80° C. for 2 h. After cooling to RT, 2 ml of 37% strength hydrochloric acid are added to the reaction mixture, whose temperature rises to 65° C. After addition of 2.6 ml of water, the reaction mixture is cooled back to RT. After addition of a further 5 ml of water, the mixture is washed with 5 ml of ethyl acetate and made alkaline by addition of 40% strength sodium hydroxide solution. Yellow crystals precipitate, and these are filtered off with suction, washed with 10 ml of water and 10 ml of diethyl ether and then dried under reduced pressure. The filtrate is concentrated using a rotary evaporator and stirred with a little water. The resulting crystals are filtered off with suction, washed with in each case 10 ml of water and diethyl ether and dried under reduced pressure.

Yield: 0.38 g (13% of theory)

$^1$H-NMR (400 MHz, DMSO-d$_6$): δ=10.77 (br. s, 1H), 7.39 (d, 2H), 7.09 (d, 2H), 6.92 (br. s, 2H), 4.30 (t, 2H), 3.21 (br. s, 2H), 2.64 (s, 6H).

LC-MS (Method 3): $R_t$=0.83 min; MS (ESIpos): m/z=340 [M+H]$^+$.

Example 35A 2-(4-Formylphenoxy)ethyl 4-methylphenylsulphonate

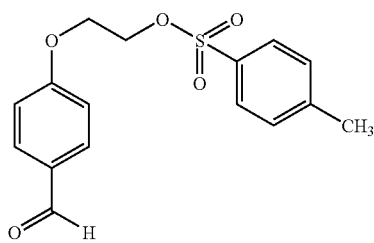 [SMILES: Cc1ccc(S(=O)(=O)OCCOc2ccc(C=O)cc2)cc1]

At RT, 12.6 ml (90.3 mmol) of triethylamine and a solution of 13.77 g (72.2 mmol) of toluene-4-sulphonyl chloride in 200 ml of dichloromethane are successively added dropwise with stirring to a solution of 10.0 g (60.2 mmol) of 4-(2-hydroxyethoxy)benzaldehyde in 300 ml of dichloromethane. The reaction mixture is stirred at RT for 12 h. After addition of 0.15 g (1.2 mmol) of 4-N,N-dimethylaminopyridine, the mixture is stirred at RT for another 4 h. 250 ml of saturated aqueous sodium bicarbonate solution are then added, and the mixture is extracted three times with in each case 100 ml of dichloromethane. The combined organic phases are dried over sodium sulphate. After removal of the solvent on a rotary evaporator, the crude product is purified chromatographically on silica gel 60 (mobile phase gradient cyclohexane→ethyl acetate).

Yield: 12.34 g (64% of theory)

HPLC (Method 6): $R_t$=4.57 min; MS (ESIpos): m/z=321 [M+H]$^+$.

Example 36A 4-(2-Azidoethoxy)benzaldehyde

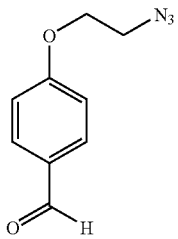 [SMILES: [N-]=[N+]=NCCOc1ccc(C=O)cc1]

A solution of 5.0 g (15.61 mmol) of the compound from Example 35A and 2.03 g (31.22 mmol) of sodium azide in 100 ml of dry DMF is stirred at RT for 12 h. The reaction mixture is concentrated using a rotary evaporator, and the residue is suspended in about 20 ml of water. After three extractions with in each case 30 ml of diethyl ether, the combined organic phases are washed twice with in each case 10 ml of water and once with 10 ml of saturated sodium chloride solution. After drying over sodium sulphate, the solvent is removed on a rotary evaporator.

Yield: 3.02 g (98% of theory)

HPLC (Method 7): $R_t$=4.14 min; MS (DCI): m/z=209 $[M+NH_4]^+$.

Example 37A

[4-(2-Azidoethoxy)benzylidene]malononitrile

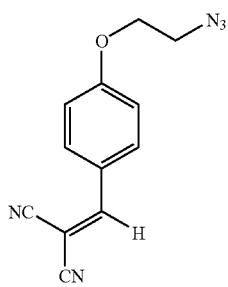

47 µl (0.47 mmol) of piperidine are added dropwise to a solution of 3.02 g (15.79 mmol) of the compound from Example 36A and 1.09 g (16.42 mmol) of malonodinitrile in 100 ml of ethanol, and the reaction mixture is stirred at +78° C. for 3.5 h. During this time, the colour of the solution changes to orange-red. After cooling to RT, the solution is allowed to stand without stirring for 20 h. A colourless precipitate is formed. Using a rotary evaporator, the crude suspension is concentrated to half of its original volume, and the crystallization is completed with cooling in an ice bath. The resulting precipitate is filtered off with suction and washed twice with in each case 20 ml of ethanol and twice with in each case 20 ml of methyl tert-butyl ether.

Yield: 2.38 g (63% of theory)

MS (DCI): m/z=257 $[M+NH_4]^+$.

Example 38A

2-Amino-4-[4-(2-azidoethoxy)phenyl]-6-mercapto-pyridine-3,5-dicarbonitrile

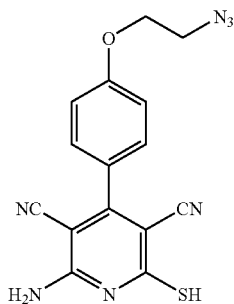

A solution of 2.39 g (9.98 mmol) of the compound from Example 37A and 2.50 g (24.92 mmol) of cyanothioacetamide in 100 ml of ethanol is stirred at +78° C. for 6 h. After cooling to RT and a further 12 h of standing without stirring, the reaction mixture is concentrated using a rotary evaporator. The residue is recrystallized from about 30 ml of ethanol. The resulting precipitate is filtered off with suction and washed twice with in each case 10 ml of methyl tert-butyl ether.

Yield: 2.04 g (61% of theory)

MS (DCI): m/z=355 $[M+NH_4]^+$.

Example 39A

2-Amino-4-[4-(2-azidoethoxy)phenyl]-6-[({2-[(4-fluorophenyl)amino]-1,3-thiazol-4-yl}methyl)thio]pyridine-3,5-dicarbonitrile

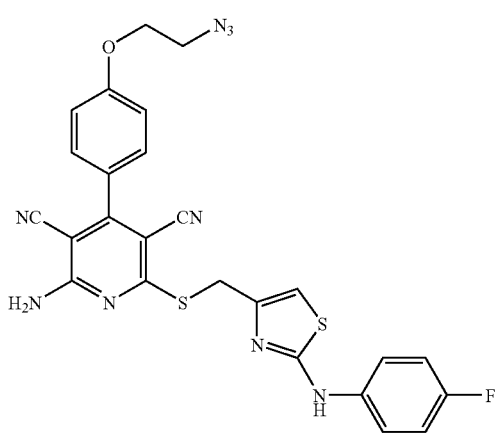

A solution of 74 mg (0.44 mmol) of 4-fluorophenylthiourea and 55 mg (0.44 mmol) of 1,3-dichloroacetone in 5 ml of ethanol is stirred at +85° C. for 60 min. After removal of the solvent on a rotary evaporator, the residue is taken up in 5 ml of DMF, 105 mg (0.31 mmol) of the compound from Example 38A and 78 mg (0.93 mmol) of sodium bicarbonate are added and the mixture is then stirred at RT for 20 h. The mixture is then added to 15 ml of saturated sodium bicarbonate solution.

The mixture is extracted with ethyl acetate (three times, 15 ml each) and the combined organic phases are dried over magnesium sulphate. After removal of the solvent on a rotary evaporator, the crude product is purified chromatographically on silica gel 60 (mobile phase gradient dichloromethane/ethanol 200:1→20:1).

Yield: 79 mg (47% of theory)

$^1$H-NMR (400 MHz, DMSO-$d_6$): δ=10.22 (s, 1H), 8.27-7.86 (br. s, 2H), 7.66-7.58 (m, 2H), 7.50 (d, 2H), 7.17-7.08 (m, 4H), 6.96 (s, 1H), 4.46 (s, 2H), 4.31-4.22 (m, 2H), 3.74-3.67 (m, 2H).

LC-MS (Method 2): $R_t$=2.72 min; MS (ESIpos): m/z=544 [M+H]$^+$.

Example 40A 4-(2-Hydroxypropoxy)benzaldehyde

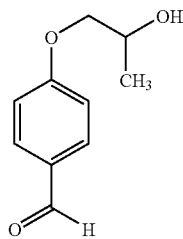

18.30 g (172.6 mmol) of sodium carbonate are added to a solution of 7.03 g (57.5 mmol) of p-hydroxybenzaldehyde and 6.80 g (71.9 mmol) of 1-chloro-2-propanol (technical grade, about 70% pure, isomer mixture with 2-chloro-1-propanol) in 125 ml of dry DMF, and the mixture is stirred at +130° C. for 20 h. After cooling to RT, 100 ml of saturated sodium bicarbonate solution are added and the mixture is extracted with ethyl acetate (three times, 100 ml each). The combined organic phases are dried over magnesium sulphate. After removal of the solvent on a rotary evaporator, the crude product is purified chromatographically on silica gel 60 (mobile phase gradient cyclohexane/ethyl acetate 5:1→2:1).

Yield: 4.60 g (44% of theory, 75:25 isomer mixture)

LC-MS (Method 4): $R_t$=1.63 min; MS (ESIpos): m/z=181 [M+H]$^+$.

Example 41A 4-(2-{[tert-Butyl(dimethyl)silyl]oxy}propoxy)benzaldehyde

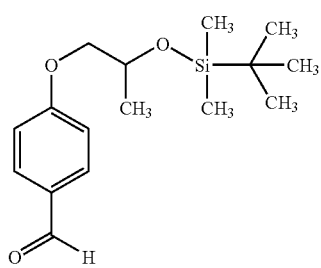 [SMILES: CC(COc1ccc(C=O)cc1)O[Si](C)(C)C(C)(C)C]

5.39 g (35.7 mmol) of tert-butyldimethylsilyl chloride and 3.30 g (48.5 mmol) of imidazole are added successively to a solution of 4.60 g (25.5 mmol) of the compound from Example 40A in 120 ml of dry dimethylformamide, and the mixture is stirred at RT for 20 h. 100 ml of saturated sodium bicarbonate solution are then added, and the reaction mixture is extracted with diethyl ether (three times, 100 ml each). The combined organic phases are dried over magnesium sulphate. After removal of the solvent on a rotary evaporator, the crude product is purified chromatographically on silica gel 60 (mobile phase gradient cyclohexane/ethyl acetate 50:1→10:1).

Yield: 4.00 g (53% of theory, 86:14 isomer mixture)

LC-MS (Method 2): $R_t$=3.29 min; MS (ESIpos): m/z=295 [M+H]$^+$.

Example 42A

2-Amino-4-[4-(2-{[tert-butyl(dimethyl)silyl]oxy}propoxy)phenyl]-6-mercaptopyridine-3,5-dicarbonitrile

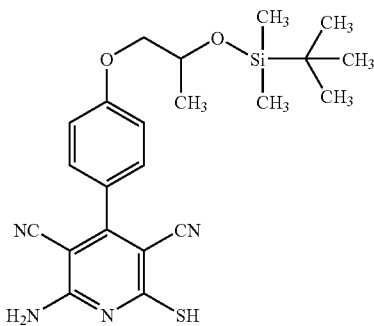

A solution of 1.77 g (5.99 mmol) of the compound from Example 41A and 1.26 g (12.59 mmol) of cyanothioacetamide in 25 ml of ethanol is stirred at +78° C. for 6 h. The mixture is then cooled to RT and stirred at this temperature for a further 20 h. The resulting precipitate is filtered off with suction and washed with cold diethyl ether. Further product is obtained from the concentrated filtrate solution by chromatographic purification on silica gel 60 (mobile phase gradient cyclohexane/ethyl acetate 1:1→1:4).

Yield: 0.25 g (9% of theory, isomer mixture)

LC-MS (Method 3): $R_t$=2.71 min, 2.77 min; MS (ESIpos): m/z=430 [M+H]$^+$.

Example 43A

2-Amino-4-[4-(2-{[tert-butyl(dimethyl)silyl]oxy}propoxy)phenyl]-6-[({2-[(4-fluorophenyl)amino]-1,3-thiazol-4-yl}methyl)thio]pyridine-3,5-dicarbonitrile

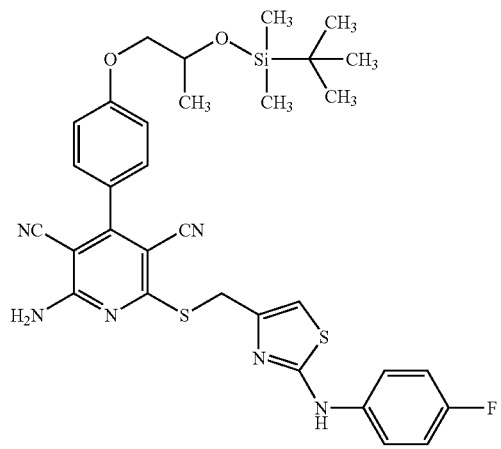

A solution of 78.6 mg (0.46 mmol) of 4-fluorophenylthiourea and 56.0 mg (0.44 mmol) of 1,3-dichloroacetone in 2 ml of dry DMF is stirred at +80° C. for 3 h. After cooling to RT, 370 mg (0.42 mmol) of the compound from Example 42A are added, and the mixture is then stirred at RT for 20 h. The reaction mixture is purified directly by two preparative HPLCs (column: YMC GEL ODS-AQ S-5/15 µm; mobile phase gradient: acetonitrile/water 10:90→95:5).

Yield: 0.44 g (14% of theory)

$^1$H-NMR (400 MHz, DMSO-$d_6$): δ=10.21 (s, 1H), 8.18-7.93 (br. s, 2H), 7.60 (dd, 2H), 7.47 (d, 2H), 7.12 (t, 2H), 7.07 (d, 2H), 6.95 (s, 1H), 4.44 (s, 2H), 4.21-4.12 (m, 1H), 3.96 (dd, 1H), 3.87 (dd, 1H), 1.18 (d, 3H), 0.87 (s, 9H), 0.08 (d, 6H).

LC-MS (Method 5): $R_t$=7.35 min; MS (ESIpos): m/z=647 [M+H]$^+$.

WORKING EXAMPLES

Example 1

2-Amino-6-[({2-[(3-chlorophenyl)amino]-1,3-thiazol-4-yl}methyl)thio]-4-[4-(2,3-dihydroxypropoxy)phenyl]pyridine-3,5-dicarbonitrile

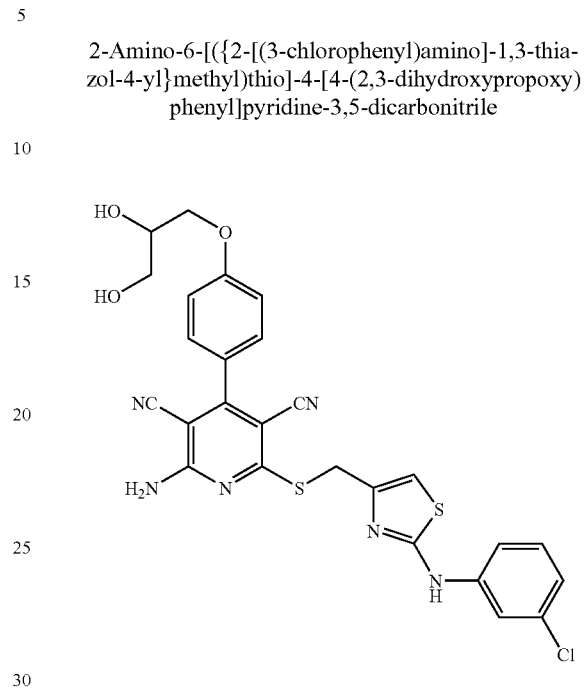

2 ml of glacial acetic acid and 90 mg (0.15 mmol) of the compound from Example 7A are added to 1 ml of water, and the mixture is stirred at RT for 16 h. The mixture is concentrated and the residue is chromatographed on silica gel 60 (mobile phase gradient dichloromethane→dichlormethane/methanol 10:1).

Yield: 30 mg (36% of theory)

m.p.: 192-194° C.

$^1$H-NMR (400 MHz, DMSO-$d_6$): δ=10.42 (s, 1H), 8.06 (br. s, 2H), 7.82 (s, 1H), 7.45 (m, 3H), 7.30 (t, 1H), 7.10 (d, 2H), 7.03 (s, 1H), 6.97 (d, 1H), 4.99 (d, 1H), 4.68 (dd, 1H), 4.49 (s, 2H), 4.09 (dd, 1H), 3.95 (dd, 1H), 3.82 (m, 1H), 3.46 (dd, 2H).

LC-MS (Method 3): $R_t$=2.17 min; MS (ESIpos): m/z=565 [M+H]$^+$.

The examples listed in Table 3 are prepared from the corresponding starting materials, analogously to Example 1:

TABLE 3
| Example No. | Structure | MS (ESI) [M + H]+ | LC-MS R_t [min] (Method) | 1H-NMR | Yield (% of theory) |
|---|---|---|---|---|---|
| 2 | 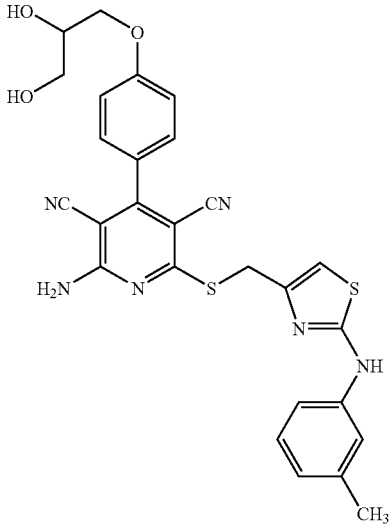 | 545 | 2.29 (2) | | 77 |
| 3 | 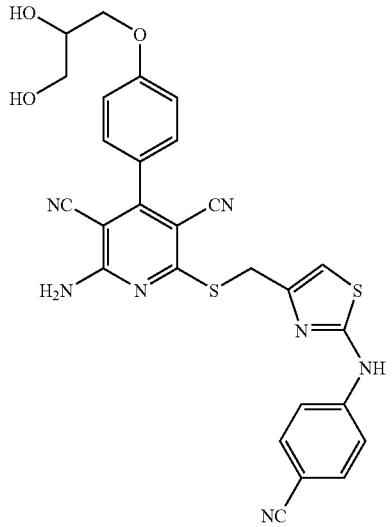 | 556 | 2.16 (2) | | 63 |
| 4 | 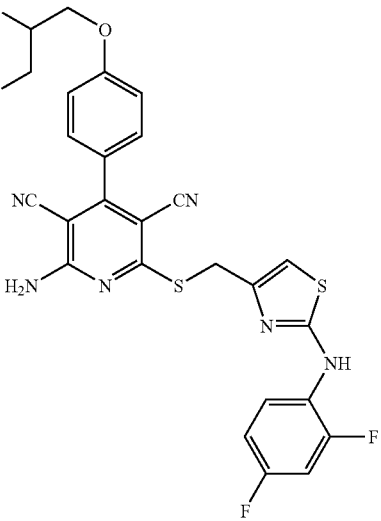 | 567 | 2.26 (2) | | 98 |

TABLE 3-continued

| Example No. | Structure | MS (ESI) [M + H]+ | LC-MS R_t [min] (Method) | 1H-NMR | Yield (% of theory) |
|---|---|---|---|---|---|
| 5 | 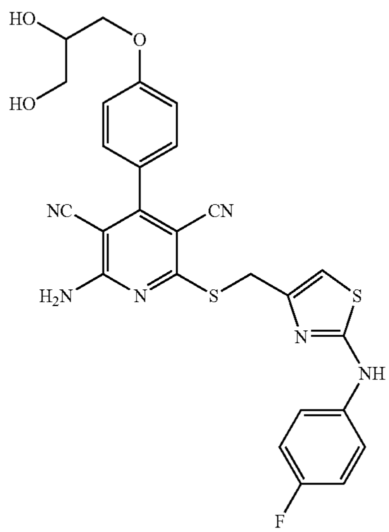 | 549 | 2.30 (4) | δ (400 MHz, DMSO-d_6) = 10.24 (s, 1H), 8.09 (br. s, 2H), 7.61 (dd, 2H), 7.46 (d, 2H), 7.18-7.05 (m, 4H), 6.97 (s, 1H), 5.00 (d, 1H), 4.70 (dd, 1H), 4.45 (s, 2H), 4.09 (dd, 1H), 3.95 (dd, 1H), 3.81 (m, 1H), 3.46 (dd, 2H). | 83 |
| 6 | 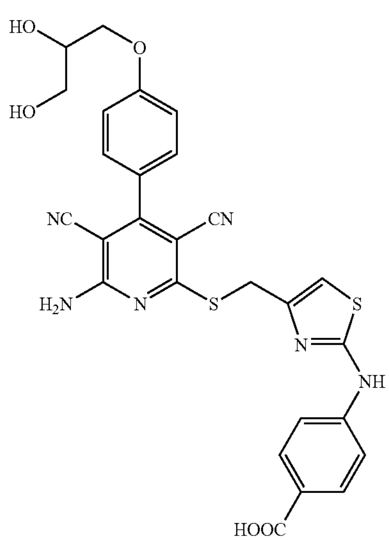 | 575 | 2.02 (4) | δ (400 MHz, DMSO-d_6) = 10.63 (s, 1H), 8.10 (br. s, 2H), 7.86 (d, 2H), 7.67 (d, 2H), 7.49 (d, 2H), 7.10 (d, 2H), 7.08 (s, 1H), 5.01 (br. s, 1H), 4.71 (br. m, 1H), 4.09 (dd, 1H), 3.95 (dd, 1H), 3.81 (m, 1H), 3.46 (d, 1H), 3.04 (m, 1H). | 67 |

TABLE 3-continued

| Example No. | Structure | MS (ESI) [M + H]+ | LC-MS R$_t$ [min] (Method) | $^1$H-NMR | Yield (% of theory) |
|---|---|---|---|---|---|
| 7 | 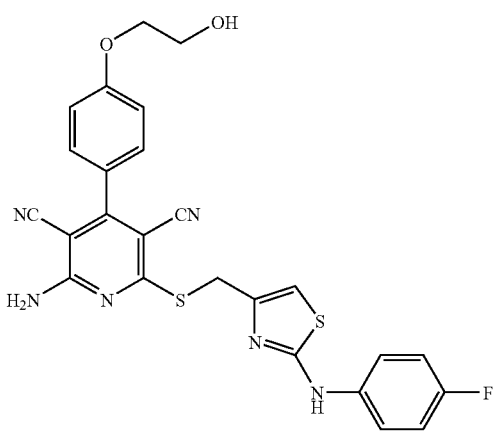 | 561 | 2.28 (4) | | 87 |

Example 8

2-Amino-6-[({2-[(4-fluorophenyl)amino]-1,3-thiazol-4-yl}methyl)thio]-4-[4-(2-hydroxyethoxy)-phenyl]pyridine-3,5-dicarbonitrile 244 mg (1.92 mmol) of 1,3-dichloroacetone are added to a solution of 327 mg (1.92 mmol) of 4-fluorophenylthiourea in 8 ml of ethanol, and the mixture is stirred under reflux for 1 h. The mixture is concentrated, the residue is dissolved in 4 ml of DMF, 429 mg (1.37 mmol) of 2-amino-4-[4-(2-hydroxyethoxy)phenyl]-6-mercaptopyridine-3,5-dicarbonitrile (preparation see WO 03/053441, Example 6/Method 1, Step 1) and 346 mg (4.1 mmol) of sodium bicarbonate are added and the mixture is stirred at RT overnight. After addition of water, the precipitate is decanted off and the residue is triturated with dichloromethane. After chromatography on silica gel (mobile phase dichloromethane/methanol 50:1), the title compound is obtained as a yellowish solid.

Yield: 316 mg (44% of theory)
HPLC (Method 1): R$_t$=4.24 min
$^1$H-NMR (400 MHz, DMSO-d$_6$): δ=10.23 (s, 1H), 8.1 (br. s, 2H), 7.62 (dd, 2H), 7.47 (d, 2H), 7.12 (dd, 4H), 6.96 (s, 1H), 4.92 (t, 1H), 4.45 (s, 2H), 4.07 (t, 2H), 3.74 (q, 2H).
LC-MS (Method 2): R$_t$=2.39 min; MS (ESIpos): m/z=519 [M+H]$^+$.

Example 9

2-Amino-6-[({2-[(4-chlorophenyl)amino]-1,3-thiazol-4-yl}methyl)thio]-4-[4-(2-hydroxyethoxy)phenyl]pyridine-3,5-dicarbonitrile

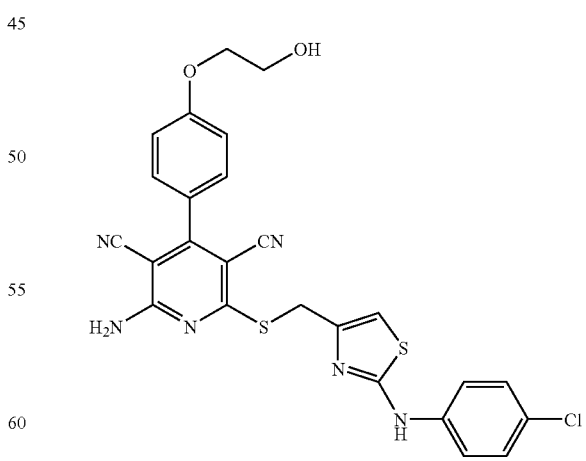

Analogously to Example 8, the title compound is obtained by reacting 179 mg (0.96 mmol) of 4-chlorophenylthiourea with 122 mg (0.96 mmol) of 1,3-dichloroacetone in ethanol, followed by reaction with 150 mg (0.48 mmol) of 2-amino-4-[4-(2-hydroxyethoxy)phenyl]-6-mercaptopyridine-3,5-dicarbonitrile.

Yield: 60 mg (12% of theory)

HPLC (Method 1): $R_t$=4.44 min $^1$H-NMR (400 MHz, DMSO-$d_6$): δ=10.37 (s, 1H), 8.1 (br. s, 2H), 7.63 (d, 2H), 7.47 (d, 2H), 7.32 (d, 2H), 7.11 (d, 2H), 6.99 (s, 1H), 4.47 (s, 2H), 4.08 (t, 2H), 3.75 (q, 2H).

LC-MS (Method 3): $R_t$=2.31 min; MS (ESIpos): m/z=535 [M+H]$^+$.

Example 10

2-Amino-6-[({2-[(2,4-difluorophenyl)amino]-1,3-thiazol-4-yl}methyl)thio]-4-[4-(2-hydroxyethoxy)phenyl]pyridine-3,5-dicarbonitrile

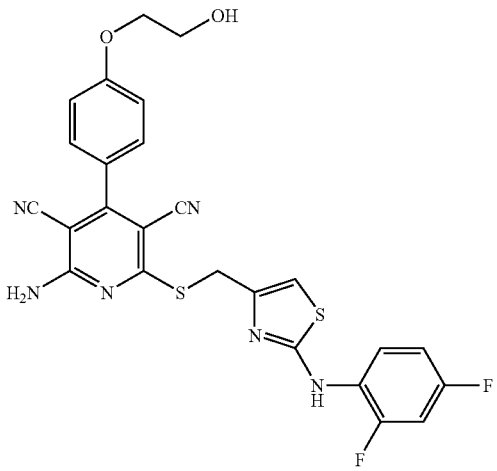

Analogously to Example 8, the title compound is obtained by reacting 169 mg (0.90 mmol) of 2,4-difluorophenylthiourea with 114 mg (0.90 mmol) of 1,3-dichloroacetone in ethanol, followed by reaction with 200 mg (0.64 mmol) of 2-amino-4-[4-(2-hydroxyethoxy)phenyl]-6-mercaptopyridine-3,5-dicarbonitrile.

Yield: 126 mg (36% of theory)

HPLC (Method 1): $R_t$=4.31 min $^1$H-NMR (400 MHz, DMSO-$d_6$): δ=9.97 (s, 1H), 8.34 (dt, 1H), 8.1 (br. s, 2H), 7.47 (d, 2H), 7.30 (dq, 1H), 7.10 (d, 2H), 7.04 (br. t, 1H), 6.99 (s, 1H), 4.91 (t, 1H), 4.45 (s, 2H), 4.06 (t, 2H), 3.74 (q, 2H).

LC-MS (Method 3): $R_t$=2.21 min; MS (ESIpos): m/z=537 [M+H]$^+$.

Example 11

2-Amino-6-[({2-[(3-fluorophenyl)amino]-1,3-thiazol-4-yl}methyl)thio]-4-[4-(2-hydroxyethoxy)phenyl]pyridine-3,5-dicarbonitrile

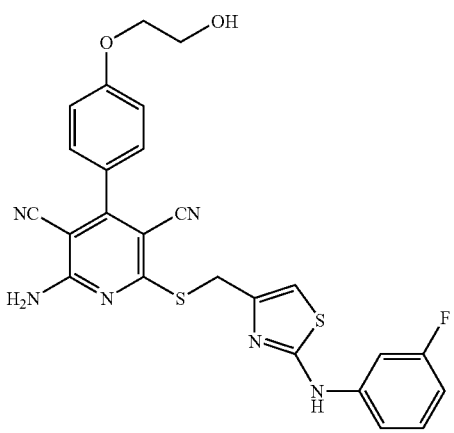

Analogously to Example 8, the title compound is obtained by reacting 153 mg (0.90 mmol) of 3-fluorophenylthiourea with 114 mg (0.90 mmol) of 1,3-dichloroacetone in ethanol, followed by reaction with 200 mg (0.64 mmol) of 2-amino-4-[4-(2-hydroxyethoxy)phenyl]-6-mercaptopyridine-3,5-dicarbonitrile.

Yield: 80 mg (24% of theory)

HPLC (Method 1): $R_t$=4.36 min $^1$H-NMR (400 MHz, DMSO-$d_6$): δ=10.46 (s, 1H), 8.1 (br. s, 2H), 7.66 (dt, 1H), 7.47 (d, 2H), 7.35-7.21 (m, 2H), 7.10 (t, 2H), 7.04 (s, 1H), 6.74 (dt, 1H), 4.92 (br. s, 1H), 4.48 (s, 2H), 4.07 (t, 2H), 3.74 (t, 2H).

LC-MS (Method 3): $R_t$=2.20 min; MS (ESIpos): m/z=519 [M+H]$^+$.

Example 12

2-Amino-6-[({2-[(2-fluorophenyl)amino]-1,3-thiazol-4-yl}methyl)thio]-4-[4-(2-hydroxyethoxy)phenyl]pyridine-3,5-dicarbonitrile

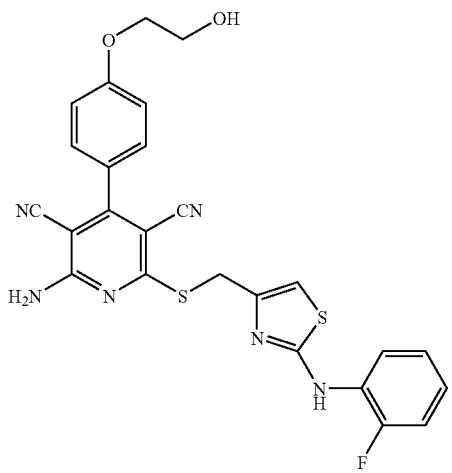

Analogously to Example 8, the title compound is obtained by reacting 153 mg (0.90 mmol) of 2-fluorophenylthiourea with 114 mg (0.90 mmol) of 1,3-dichloroacetone in ethanol, followed by reaction with 200 mg (0.64 mmol) of 2-amino-4-[4-(2-hydroxyethoxy)phenyl]-6-mercaptopyridine-3,5-dicarbonitrile.

Yield: 170 mg (51% of theory)

HPLC (Method 1): $R_t$=4.28 min $^1$H-NMR (400 MHz, DMSO-$d_6$): δ=9.99 (s, 1H), 8.36 (t, 1H), 8.1 (br. s, 2H), 7.46 (d, 2H), 7.22 (dd, 1H), 7.16-7.08 (m, 3H), 7.02-6.96 (m, 2H), 4.90 (t, 1H), 4.46 (s, 2H), 4.07 (t, 2H), 3.74 (t, 2H).

LC-MS (Method 3): $R_t$=2.16 min; MS (ESIpos): m/z=519 [M+H]$^+$.

Example 13

4-({4-[({6-Amino-3,5-dicyano-4-[4-(2-hydroxy-ethoxy)phenyl]pyridin-2-yl}thio)methyl]-1,3-thiazol-2-yl}amino)benzoic acid

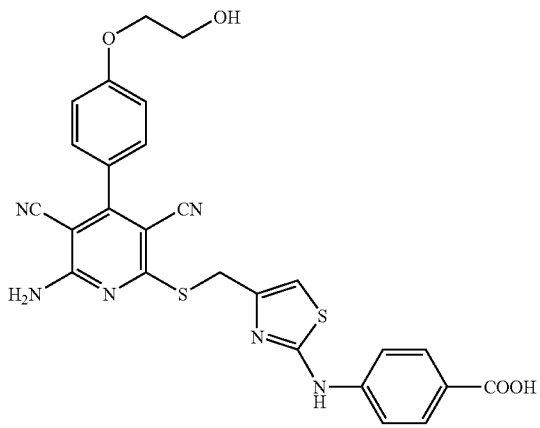

Analogously to Example 8, the title compound is obtained by reacting 176 mg (0.90 mmol) of 4-[(aminocarbonothioyl)amino]benzoic acid with 114 mg (0.90 mmol) of 1,3-dichloroacetone in ethanol, followed by reaction with 200 mg (0.64 mmol) of 2-amino-4-[4-(2-hydroxyethoxy)phenyl]-6-mercaptopyridine-3,5-dicarbonitrile.

Yield: 45 mg (13% of theory)
HPLC (Method 1): $R_t$=3.81 min
$^1$H-NMR (300 MHz, DMSO-$d_6$): δ=12.6 (br. s, 1H), 10.64 (s, 1H), 8.1 (br. s, 2H), 7.87 (d, 2H), 7.68 (d, 2H), 7.49 (d, 2H), 7.13-7.06 (m, 3H), 4.45 (s, 2H), 4.07 (t, 2H), 3.74 (t, 2H).
LC-MS (Method 2): $R_t$=1.97 min; MS (ESIpos): m/z=545 [M+H]$^+$.

In this reaction, ethyl 4-({4-[({6-amino-3,5-dicyano-4-[4-(2-hydroxyethoxy)phenyl]pyridin-2-yl}thio)methyl]-1,3-thiazol-2-yl}amino)benzoate (see Example 14) is obtained as by-product.

Example 14

Ethyl 4-({4-[({6-amino-3,5-dicyano-4-[4-(2-hydroxyethoxy)phenyl]pyridin-2-yl}thio)methyl]-1,3-thiazol-2-yl}amino)benzoate

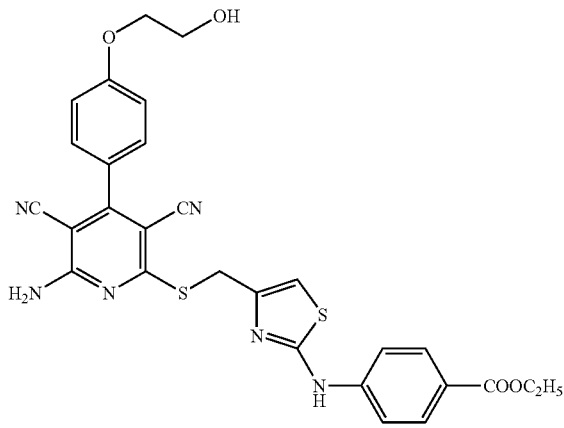

As described in Example 13, the title compound is obtained as a by-product in the reaction of 176 mg (0.90 mmol) of 4-[(aminocarbonothioyl)amino]benzoic acid with 114 mg (0.90 mmol) of 1,3-dichloroacetone in ethanol and subsequent reaction with 200 mg (0.64 mmol) of 2-amino-4-[4-(2-hydroxyethoxy)phenyl]-6-mercaptopyridine-3,5-dicarbonitrile.

Yield: 59 mg (16% of theory)
HPLC (Method 1): $R_t$=4.32 min
$^1$H-NMR (300 MHz, DMSO-$d_6$): δ=10.67 (s, 1H), 8.1 (br. s, 2H), 7.88 (d, 2H), 7.68 (d, 2H), 7.47 (d, 2H), 7.13-7.07 (m, 3H), 4.91 (br. s, 1H), 4.50 (s, 2H), 4.26 (q, 2H), 4.07 (t, 2H), 3.74 (t, 2H), 1.29 (t, 3H).
LC-MS (Method 2): $R_t$=2.46 min; MS (ESIpos): m/z=573 [M+H]$^+$.

Example 15

2-Amino-4-[4-(2-hydroxyethoxy)phenyl]-6-[({2-[(4-nitrophenyl)amino]-1,3-thiazol-4-yl}methyl)-thio]pyridine-3,5-dicarbonitrile

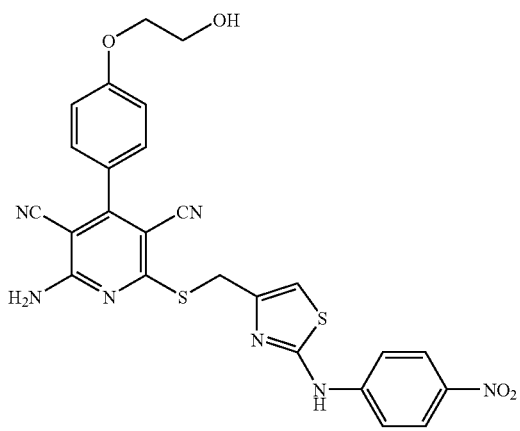

Analogously to Example, 8, the title compound is obtained by reacting 177 mg (0.90 mmol) of 4-nitrophenylthiourea with 114 mg (0.90 mmol) of 1,3-dichloroacetone in ethanol, followed by reaction with 200 mg (0.64 mmol) of 2-amino-4-[4-(2-hydroxyethoxy)phenyl]-6-mercaptopyridine-3,5-dicarbonitrile.

Yield: 67 mg (19% of theory)
HPLC (Method 1): $R_t$=4.23 min
$^1$H-NMR (400 MHz, DMSO-$d_6$): δ=11.03 (s, 1H), 8.20 (d, 2H), 8.1 (br. s, 2H), 7.80 (d, 2H), 7.48 (d, 2H), 7.20 (s, 1H), 7.10 (d, 2H), 4.90 (t, 1H), 4.52 (s, 2H), 4.07 (t, 2H), 3.74 (q, 2H).
LC-MS (Method 2): $R_t$=2.39 min; MS (ESIpos): m/z=546 [M+H]$^+$.

Example 16

2-Amino-4-[4-(2-hydroxyethoxy)phenyl]-6-{[(2-{[3-(trifluoromethyl)phenyl]amino}-1,3-thiazol-4-yl)methyl]thio}pyridine-3,5-dicarbonitrile

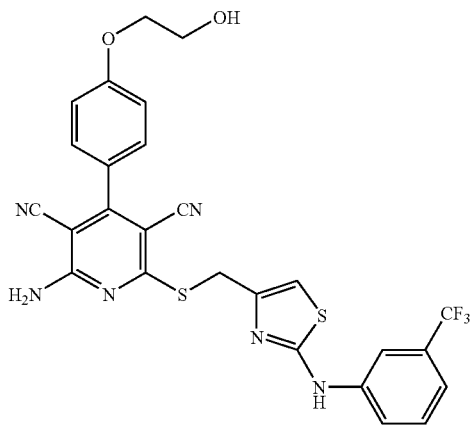

A solution of 25.4 mg (0.2 mmol) of 1,3-dichloroacetone in 0.5 ml of DMF is added to 44 mg (0.2 mmol) of 3-trifluoromethylthiourea. The reaction mixture is stirred at 80° C. for 3 h. After cooling, 62.5 mg (0.2 mmol) of 2-amino-4-[4-(2-hydroxyethoxy)phenyl]-6-mercaptopyridine-3,5-dicarbonitrile in 0.2 ml of DMF and 67 mg (0.8 mmol) of sodium bicarbonate are added. The reaction mixture is stirred at RT overnight and then filtered and purified by preparative HPLC (column: GROMSIL 1200DS-HE-4, 5 μm, 20×50 mm; UV detection: 220 nm; injection volume 700 μl; mobile phase A: water+ 0.1% formic acid, mobile phase B: acetonitrile; gradient: 0 min 10% B→1.5 min 10% B→5.5 min 90% B→7 min 90% B→7.1 min 10% B→8 min 10% B; flow rate: 25 ml/min). The product-containing fractions are concentrated under reduced pressure.

Yield: 71.6 mg (63% of theory)
LC-MS (Method 2): $R_t$=2.56 min; MS (ESIpos): m/z=569 [M+H]$^+$.

$^1$H-NMR (400 MHz, DMSO-d$_6$): δ=10.6 (s, 1H), 8.1 (s, 1H), 8.1 (br. s, 2H), 7.8 (d, 1H), 7.5 (m, 3H), 7.25 (d, 1H), 7.1 (m, 3H), 4.9 (t, 1H), 4.5 (s, 2H), 4.1 (t, 2H), 3.75 (q, 2H).

Analogously to Example 16, Examples 17 to 28, listed in Table 4, are prepared from 2-amino-4-[4-(2-hydroxyethoxy)phenyl]-6-mercaptopyridine-3,5-dicarbonitrile (Examples 17 to 25) and from 2-amino-4-[4-(2-methoxyethoxy)phenyl]-6-mercaptopyridine-3,5-dicarbonitrile (preparation see WO 03/053441, Example 1/Step 2) (Examples 26 to 28), respectively:

TABLE 4

| Example No. | Structure | MS (ESI) [M + H]$^+$ | LC-MS $R_t$ [min] (Method) | Yield (% of theory) |
|---|---|---|---|---|
| 17 | 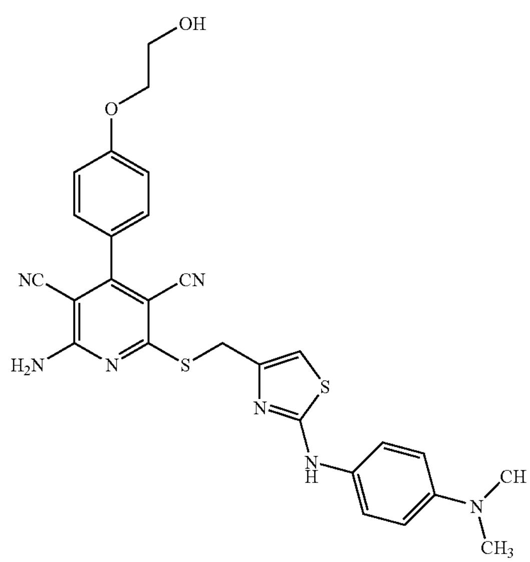 | 544 | 1.81 (2) | 29 |

TABLE 4-continued

| Example No. | Structure | MS (ESI) [M + H]+ | LC-MS R_t [min] (Method) | Yield (% of theory) |
|---|---|---|---|---|
| 18 | 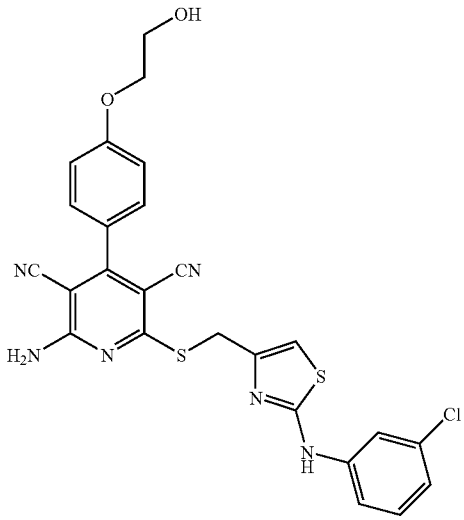 | 536 | 2.5 (2) | 65 |
| 19 | 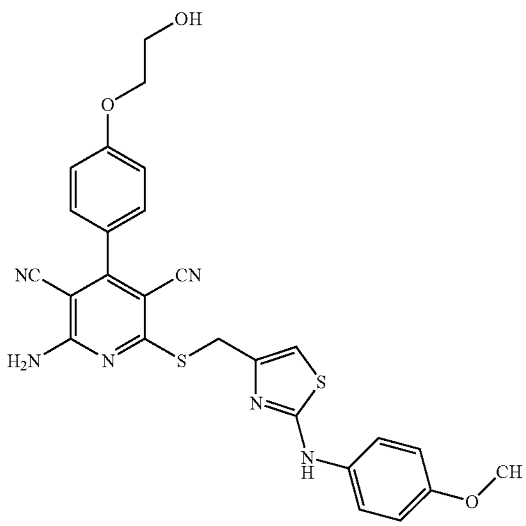 | 531 | 2.28 (2) | 65 |
| 20 | 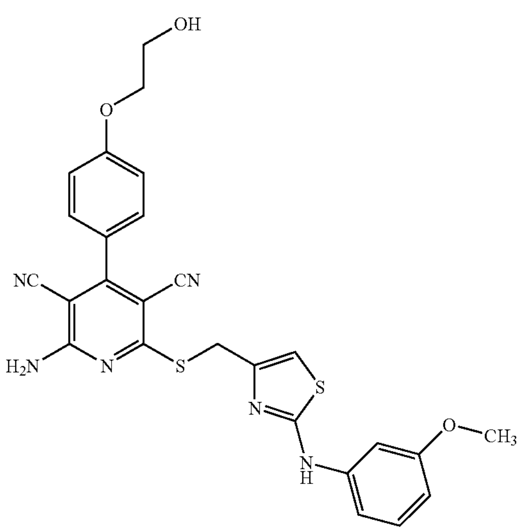 | 531 | 2.35 (2) | 76 |

TABLE 4-continued

| Example No. | Structure | MS (ESI) [M + H]+ | LC-MS $R_t$ [min] (Method) | Yield (% of theory) |
|---|---|---|---|---|
| 21 | 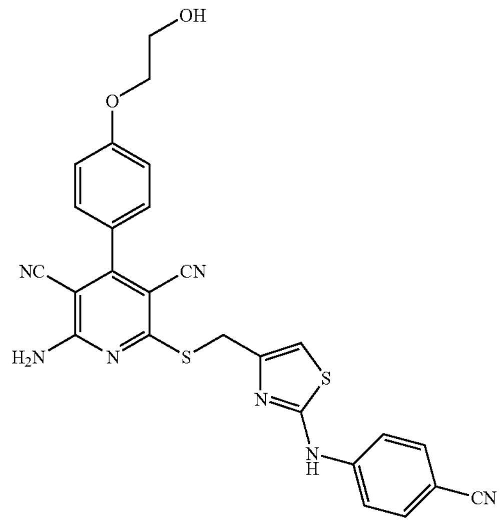 | 526 | 2.31 (2) | 32 |
| 22 | 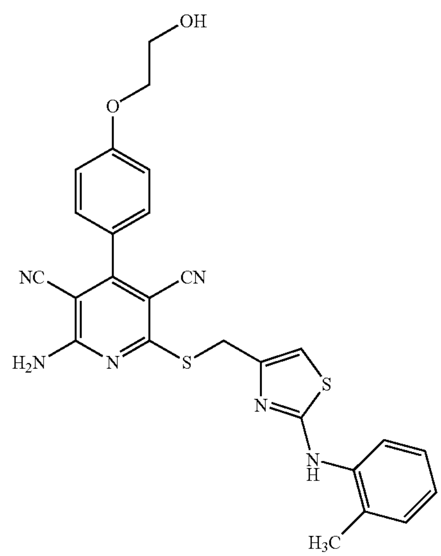 | 515 | 2.36 (2) | 77 |
| 23 | 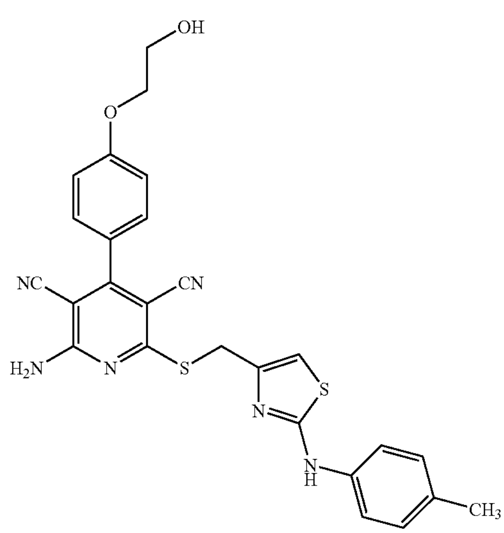 | 515 | 2.44 (2) | 64 |

TABLE 4-continued

| Example No. | Structure | MS (ESI) [M + H]+ | LC-MS Rt [min] (Method) | Yield (% of theory) |
|---|---|---|---|---|
| 24 | 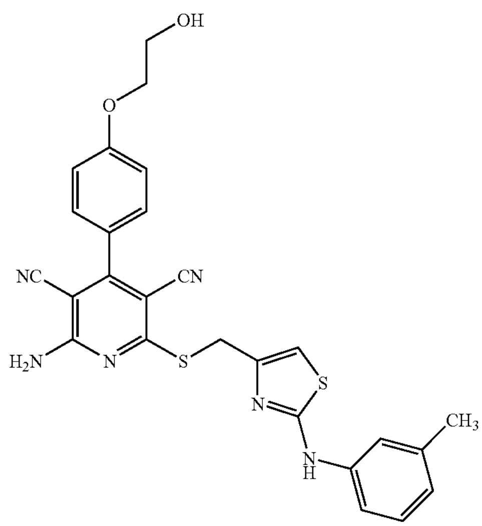 | 515 | 2.44 (2) | 78 |
| 25 | 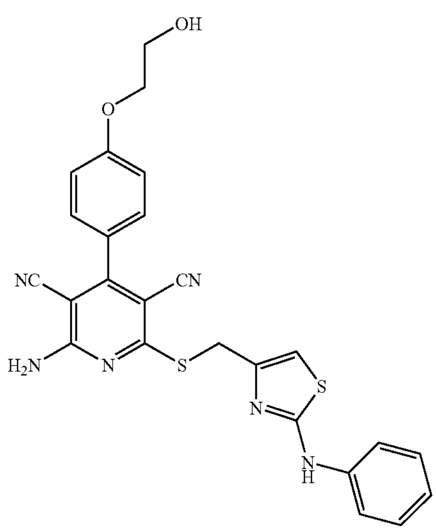 | 501 | 2.35 (2) | 70 |
| 26 | 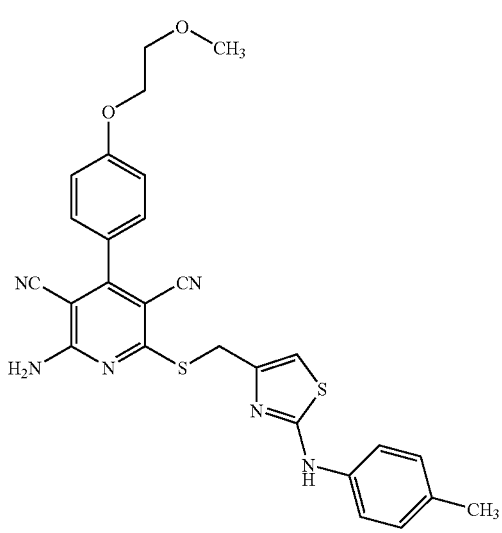 | 529 | 2.74 (4) | 27 |

TABLE 4-continued

| Example No. | Structure | MS (ESI) [M + H]+ | LC-MS R_t [min] (Method) | Yield (% of theory) |
|---|---|---|---|---|
| 27 | 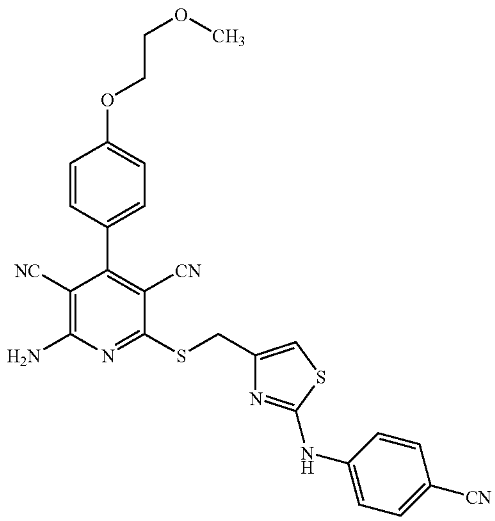 | 540 | 2.60 (4) | 51 |
| 28 | 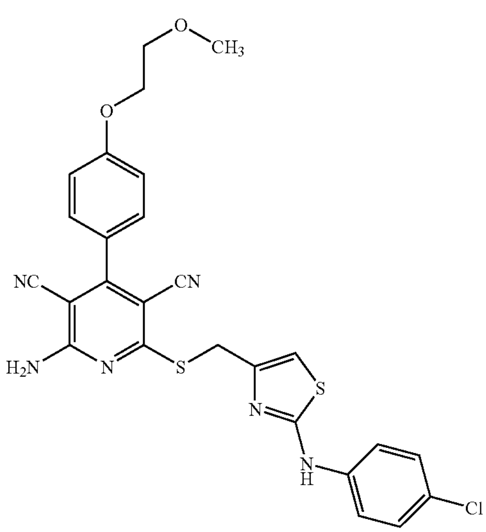 | 550 | 2.79 (2) | 12 |

The examples listed in Table 5 are prepared from the corresponding starting materials, analogously to Example 1:
TABLE 5
| Example No. | Structure | MS (ESI) [M + H]⁺ | LC-MS R$_t$ [min] (Method) | ¹H-NMR | Yield (% of theory) |
|---|---|---|---|---|---|
| 29 | 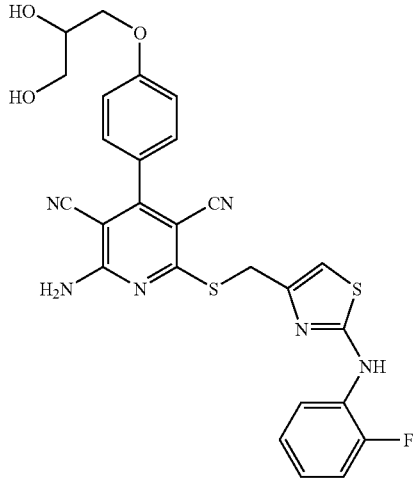 | 549 | 2.25 (4) | δ (400 MHz, DMSO-d$_6$) = 10.00 (s, 1H), 8.37 (t, 1H), 8.07 (br. s, 2H), 7.47 (d, 2H), 7.23 (m, 1H), 7.12 (m, 3H), 6.99 (m, 2H), 4.47 (s, 2H), 4.09 (dd, 1H), 3.95 (dd, 1H), 3.82 (m, 1H), 3.46 (dd, 2H). | 68 |
| 30 | 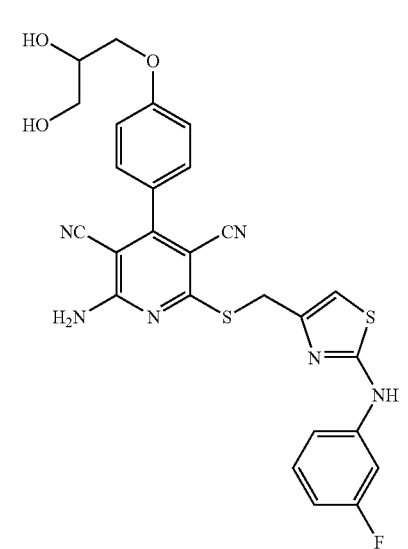 | 549 | 2.32 (4) | δ (400 MHz, DMSO-d$_6$) = 10.42 (s, 1H), 8.06 (br. s, 2H), 7.82 (s, 1H), 7.45 (m, 3H), 7.30 (t, 1H), 7.10 (d, 2H), 7.03 (s, 1H), 6.74 (dt, 1H), 4.49 (s, 2H), 4.08 (dd, 1H), 3.95 (dd, 1H), 3.82 (m, 1H), 3.46 (dd, 2H). | 60 |

TABLE 5-continued

| Example No. | Structure | MS (ESI) [M + H]⁺ | LC-MS R$_t$ [min] (Method) | ¹H-NMR | Yield (% of theory) |
|---|---|---|---|---|---|
| 31 | 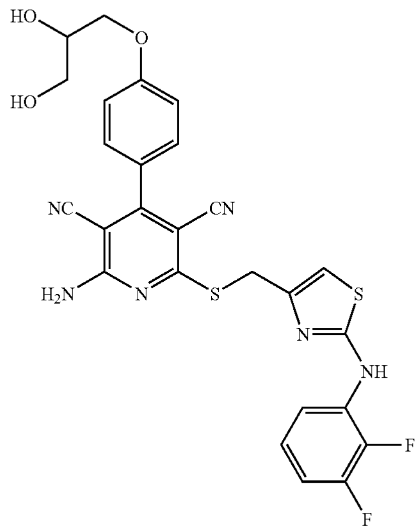 | 567 | 2.32 (4) | δ (400 MHz, DMSO-d$_6$) = 10.23 (s, 1H), 8.22 (t, 1H), 8.07 (br. s, 2H), 7.46 (d, 2H), 7.09 (m, 4H), 6.99 (dd, 1H), 4.99 (d, 1H), 4.67 (t, 1H), 4.47 (s, 2H), 4.08 (dd, 1H), 3.95 (dd, 1H), 3.81 (m, 1H), 3.46 (t, 2H). | 75 |
| 32 | 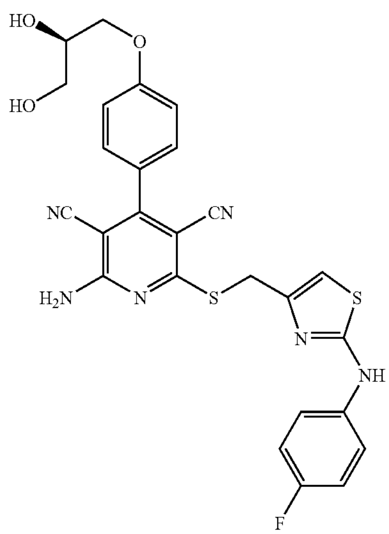 | 549 | 2.26 (4) | | 85 |
| 33 | 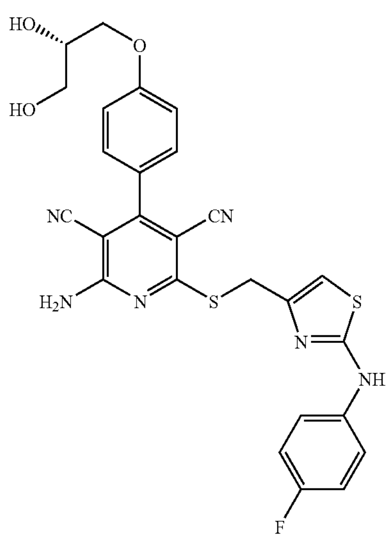 | 549 | 2.02 (3) | δ (400 MHz, DMSO-d$_6$) = 10.2 (br. s, 1H), 8.1 (br. s, 2H), 7.6-7.65 (m, 2H), 7.47 (d, 2H), 7.1-7.17 (m, 4H), 6.97 (s, 1H), 5.0 (br. s, 1H), 4.7 (br. s, 1H), 4.44 (s, 2H), 4.06-4.1 (m, 1H), 3.92-3.97 (m, 1H), 3.81 (m, 1H), 3.46 (dd, 2H). | 92 |

TABLE 5-continued

| Example No. | Structure | MS (ESI) [M + H]+ | LC-MS R_t [min] (Method) | 1H-NMR | Yield (% of theory) |
|---|---|---|---|---|---|
| 34 | 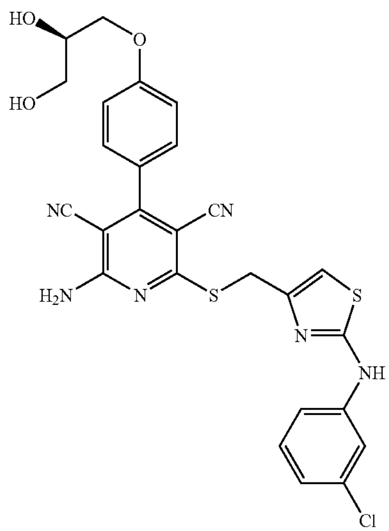 | 565 | 2.33 (2) | | 66 |
| 35 | 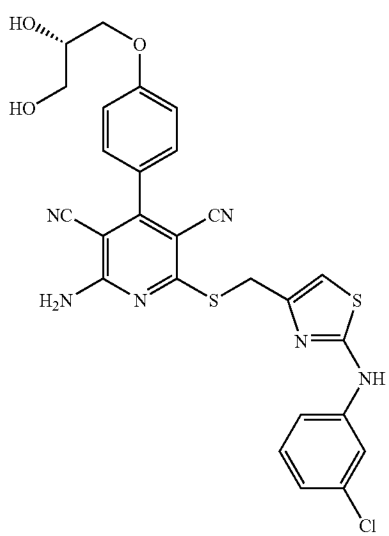 | 565 | 2.37 (4) | δ (400 MHz, DMSO-$d_6$) = 10.42 (s, 1H), 8.25-7.90 (br. s, 2H), 7.81 (s, 1H), 7.50-7.41 (m, 3H), 7.30 (t, 1H), 7.10 (d, 2H), 7.03 (s, 1H), 6.97 (s, 1H), 5.00 (d, 1H), 4.59 (t, 1H), 4.49 (s, 2H), 4.08 (dd, 1H), 3.95 (dd, 1H), 3.86-3.78 (m, 1H), 3.46 (t, 2H). | 80 |
| 36 | 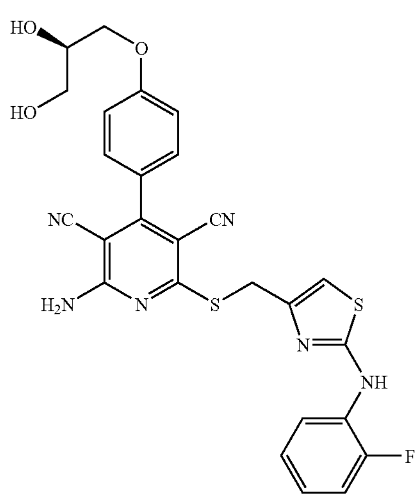 | 549 | 2.20 (2) | | 86 |

TABLE 5-continued
| Example No. | Structure | MS (ESI) [M + H]+ | LC-MS R$_t$ [min] (Method) | ¹H-NMR | Yield (% of theory) |
|---|---|---|---|---|---|
| 37 | 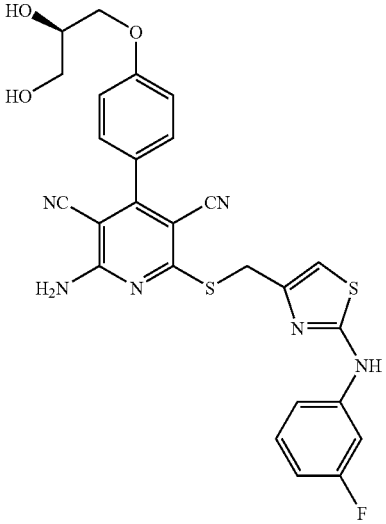 | 549 | 2.28 (4) | | 51 |
| 38 | 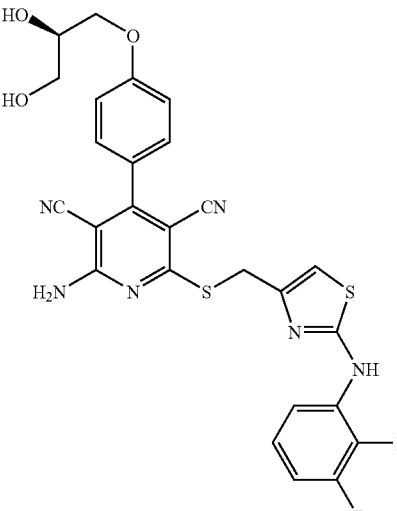 | 561 | 2.28 (4) | | 87 |

TABLE 5-continued

| Example No. | Structure | MS (ESI) [M + H]+ | LC-MS R$_t$ [min] (Method) | $^1$H-NMR | Yield (% of theory) |
|---|---|---|---|---|---|
| 39 | 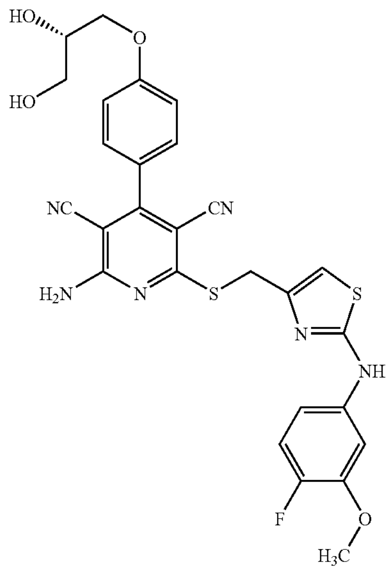 | 579 | 2.02 (3) | δ (400 MHz, DMSO-d$_6$) = 10.21 (s, 1H), 8.05 (br. s, 2H), 7.60 (dd, 1H), 7.47 (d, 2H), 7.14-7.00 (m, 4H), 6.97 (s, 1H), 4.99 (d, 1H), 4.68 (t, 1H), 4.47 (s, 2H), 4.09 (dd, 1H), 3.94 (dd, 1H), 3.86-3.78 (m, 1H), 3.80 (s, 3H), 3.46 (t, 2H). | 48 |
| 40 | 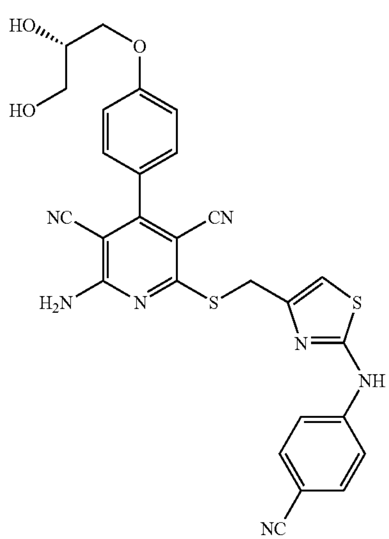 | 556 | 2.12 (2) | δ (400 MHz, DMSO-d$_6$) = 10.78 (s, 1H), 8.09 (br. s, 2H), 7.77 (dd, 4H), 7.48 (d, 2H), 7.14 (s, 1H), 7.10 (d, 2H), 4.99 (d, 1H), 4.69 (t, 1H), 4.50 (s, 2H), 4.08 (dd, 1H), 3.95 (dd, 1H), 3.86-3.77 (m, 1H), 3.47 (t, 2H). | 67 |

TABLE 5-continued

| Example No. | Structure | MS (ESI) [M + H]+ | LC-MS Rt [min] (Method) | 1H-NMR | Yield (% of theory) |
|---|---|---|---|---|---|
| 41 | 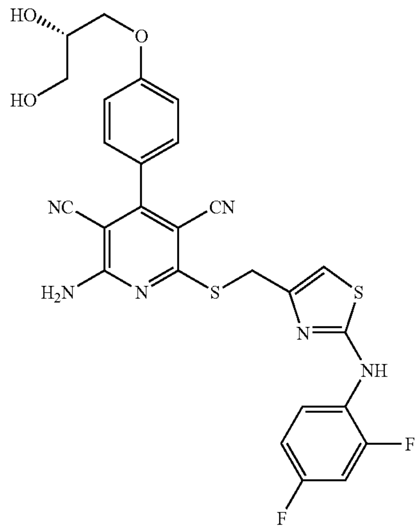 | 567 | 2.24 (2) | δ (400 MHz, DMSO-d6) = 9.96 (s, 1H), 8.48-8.28 (m, 1H), 8.08 (br. s, 2H), 7.47 (dd, 2H), 7.34-7.26 (m, 1H), 7.09 (d, 2H), 7.05 (t, 1H), 6.99 (s, 1H), 4.99 (d, 1H), 4.69 (t, 1H), 4.43 (s, 2H), 4.08 (dd, 1H), 3.95 (dd, 1H), 3.86-3.78 (m, 1H), 3.46 (t, 2H). | 99 |
| 42 | 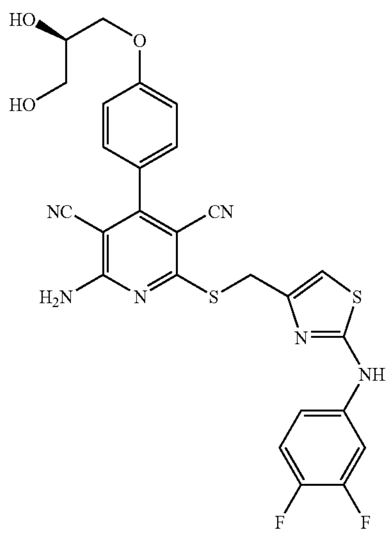 | 567 | 2.08 (3) | | 65 |
| 43 | 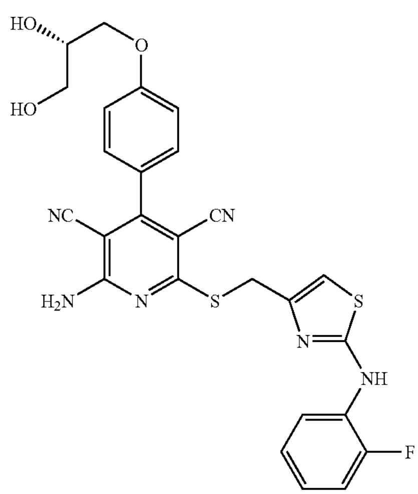 | 549 | 2.02 (3) | | 69 |

TABLE 5-continued
| Example No. | Structure | MS (ESI) [M + H]+ | LC-MS Rt [min] (Method) | 1H-NMR | Yield (% of theory) |
|---|---|---|---|---|---|
| 44 | 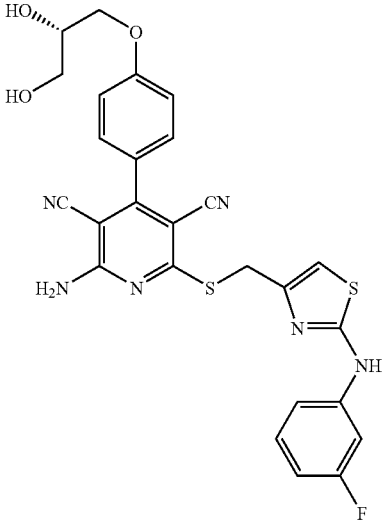 | 549 | 2.04 (3) | | 70 |
| 45 | 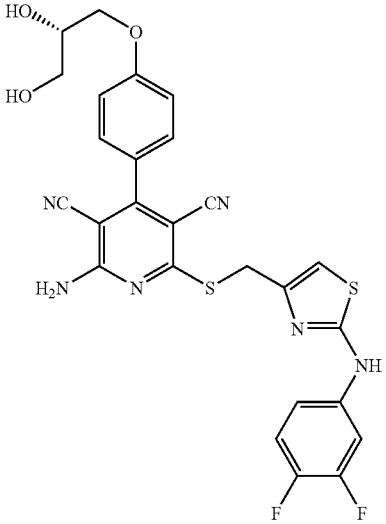 | 567 | 2.09 (3) | | 75 |
| 46 | 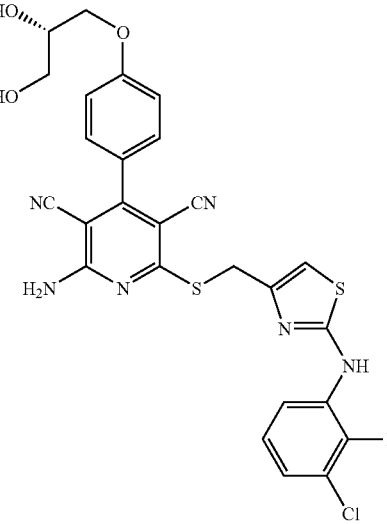 | 583 | 2.20 (3) | | 74 |

TABLE 5-continued
| Example No. | Structure | MS (ESI) [M + H]+ | LC-MS R_t [min] (Method) | 1H-NMR | Yield (% of theory) |
|---|---|---|---|---|---|
| 47 | 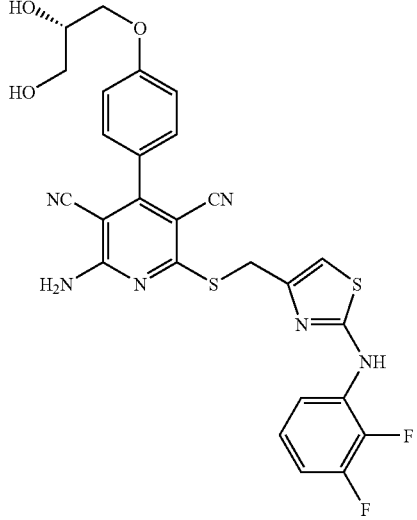 | 567 | 2.34 (4) | | 79 |
| 48 | 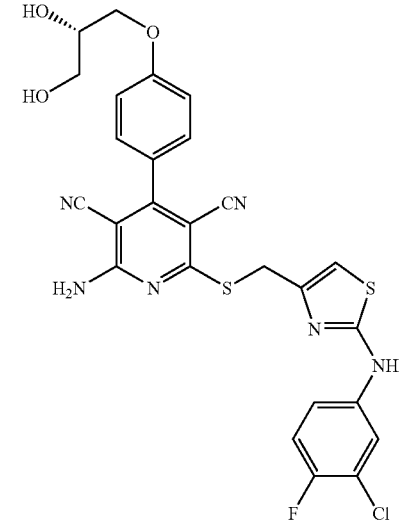 | 583 | 2.16 (3) | | 51 |

TABLE 5-continued
| Example No. | Structure | MS (ESI) [M + H]+ | LC-MS Rt [min] (Method) | 1H-NMR | Yield (% of theory) |
|---|---|---|---|---|---|
| 49 | 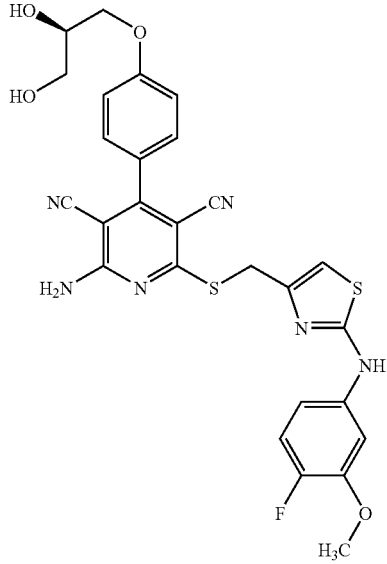 | 579 | 2.27 (4) | | 76 |
| 50 | 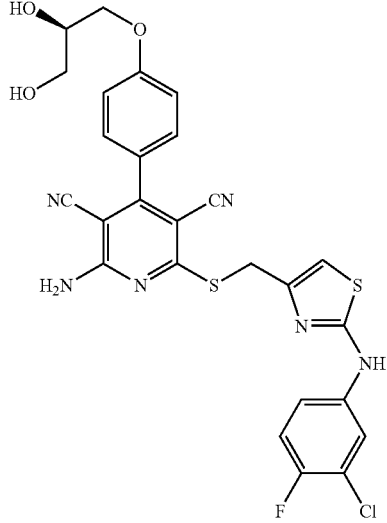 | 583 | 2.42 (4) | | 90 |

TABLE 5-continued

| Example No. | Structure | MS (ESI) [M + H]+ | LC-MS R$_t$ [min] (Method) | $^1$H-NMR | Yield (% of theory) |
|---|---|---|---|---|---|
| 51 | 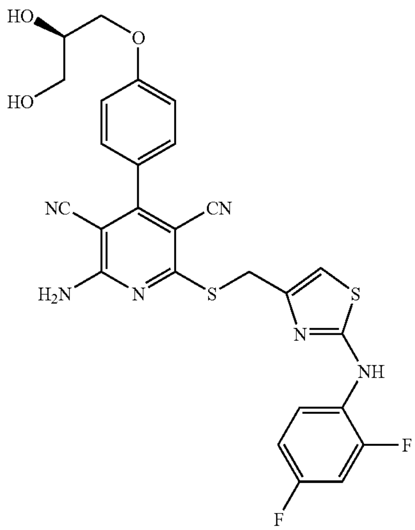 | 567 | 2.06 (3) | | 92 |
| 52 | 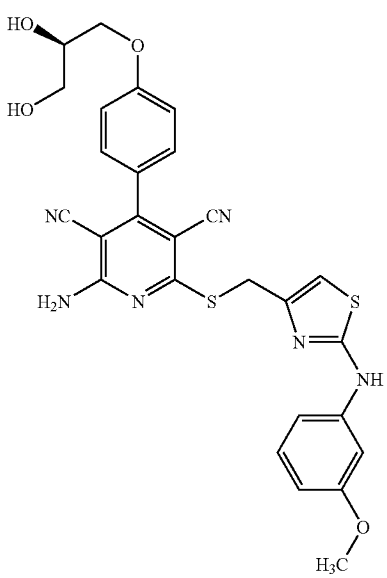 | 561 | 1.99 (3) | | 96 |

TABLE 5-continued
| Example No. | Structure | MS (ESI) [M + H]+ | LC-MS R$_t$ [min] (Method) | $^1$H-NMR | Yield (% of theory) |
|---|---|---|---|---|---|
| 53 | 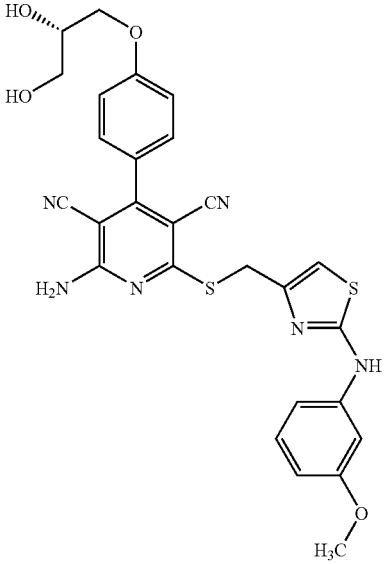 | 561 | 1.99 (3) | | 96 |
| 54 | 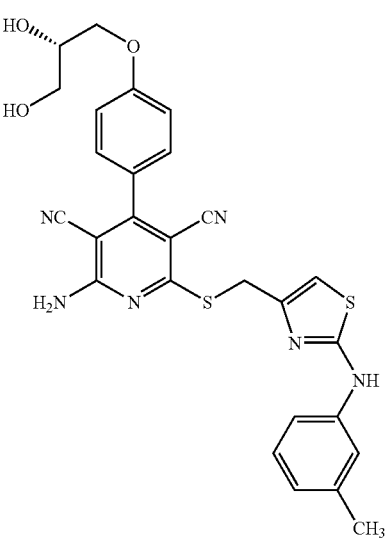 | 545 | 2.26 (2) | | 77 |

TABLE 5-continued

| Example No. | Structure | MS (ESI) [M + H]⁺ | LC-MS R_t [min] (Method) | ¹H-NMR | Yield (% of theory) |
|---|---|---|---|---|---|
| 55 | 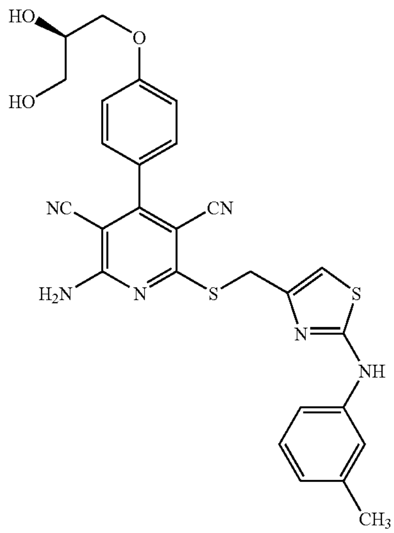 | 545 | 2.26 (2) | | 68 |
| 56 | 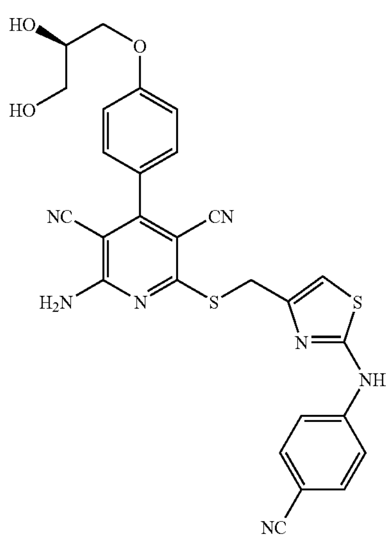 | 556 | 2.12 (2) | | 25 |

Analogously to Example 16, the examples listed in Table 6 are prepared from 2-amino-4-[4-(2-hydroxyethoxy)phenyl]-6-mercaptopyridine-3,5-dicarbonitrile:

TABLE 6
| Example No. | Structure | MS (ESI) [M + H]+ | LC-MS R$_t$ [min] (Method) | Yield (% of theory) |
|---|---|---|---|---|
| 57 | 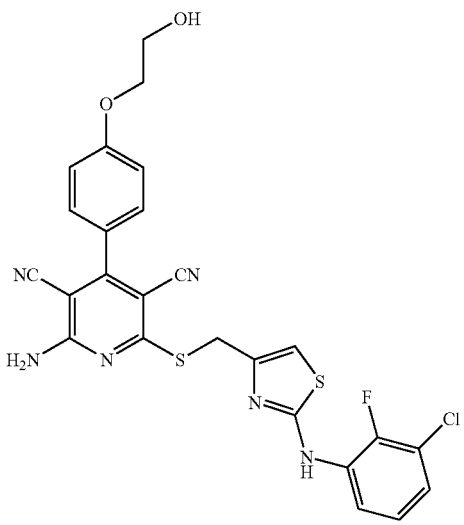 | 553 | 2.52 (2) | 68 |
| 58 | 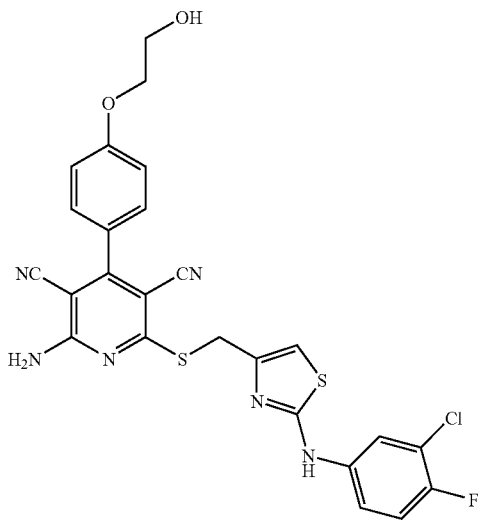 | 553 | 2.50 (2) | 42 |

TABLE 6-continued

| Example No. | Structure | MS (ESI) [M + H]⁺ | LC-MS R$_t$ [min] (Method) | Yield (% of theory) |
|---|---|---|---|---|
| 59 | 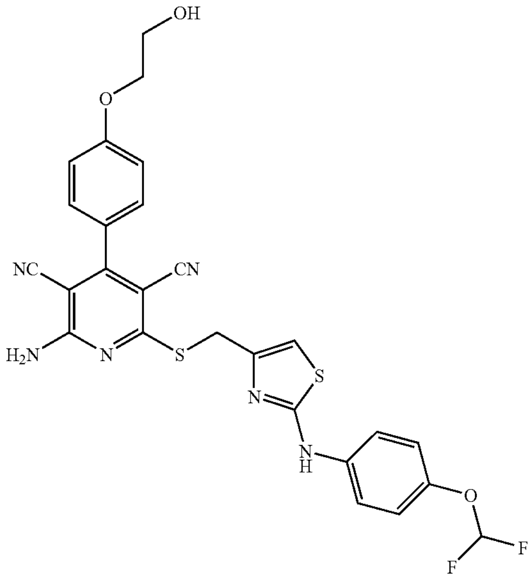 | 566 | 2.24 (3) | 20 |
| 60 | 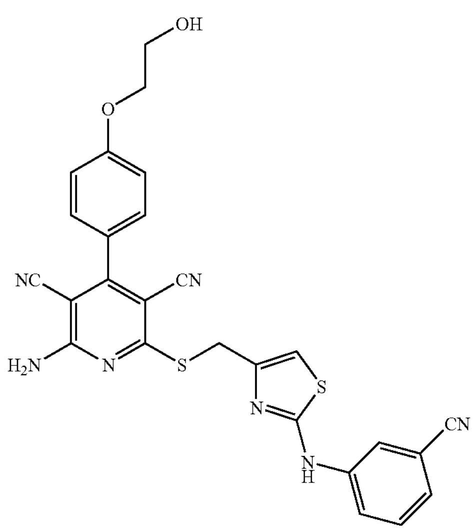 | 526 | 2.10 (3) | 83 |

TABLE 6-continued
| Example No. | Structure | MS (ESI) [M + H]⁺ | LC-MS R$_t$ [min] (Method) | Yield (% of theory) |
|---|---|---|---|---|
| 61 | 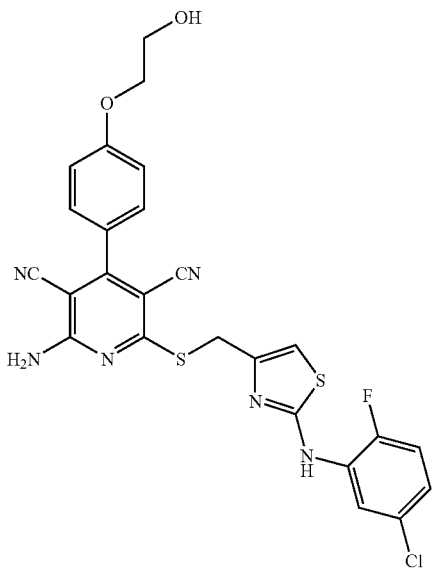 | 553 | 2.48 (2) | 70 |
| 62 | 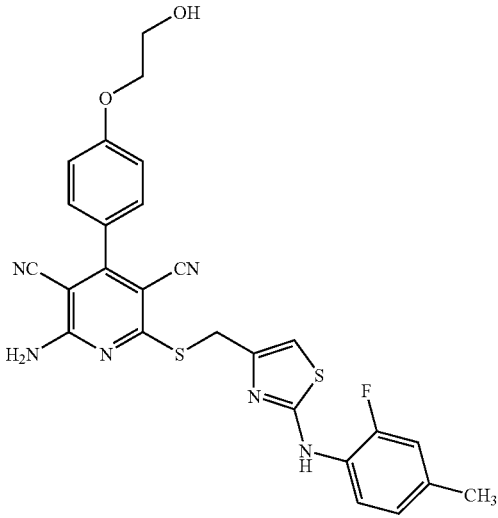 | 533 | 2.45 (2) | 70 |

TABLE 6-continued
| Example No. | Structure | MS (ESI) [M + H]+ | LC-MS Rt [min] (Method) | Yield (% of theory) |
|---|---|---|---|---|
| 63 | 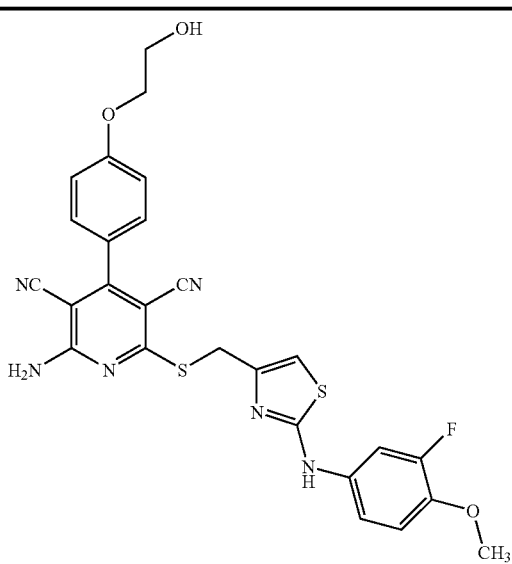 | 549 | 2.12 (3) | 66 |
| 64 | 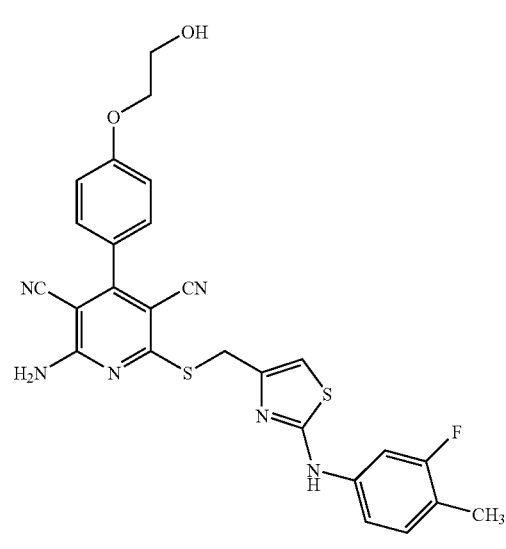 | 533 | 2.48 (2) | 54 |

TABLE 6-continued
| Example No. | Structure | MS (ESI) [M + H]+ | LC-MS $R_t$ [min] (Method) | Yield (% of theory) |
|---|---|---|---|---|
| 65 | 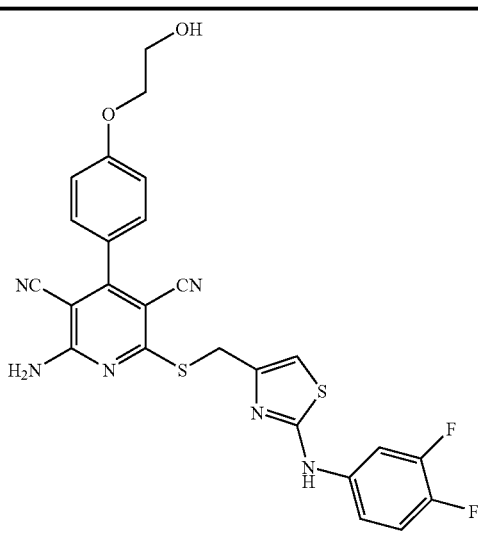 | 537 | 2.43 (2) | 34 |
| 66 | 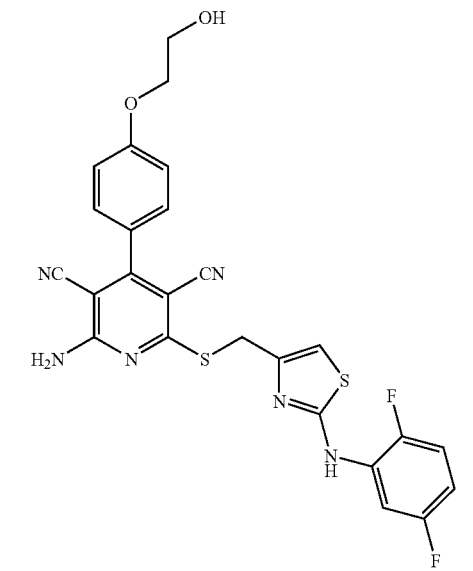 | 537 | 2.22 (3) | 16 |

TABLE 6-continued

| Example No. | Structure | MS (ESI) [M + H]+ | LC-MS R$_t$ [min] (Method) | Yield (% of theory) |
|---|---|---|---|---|
| 67 | 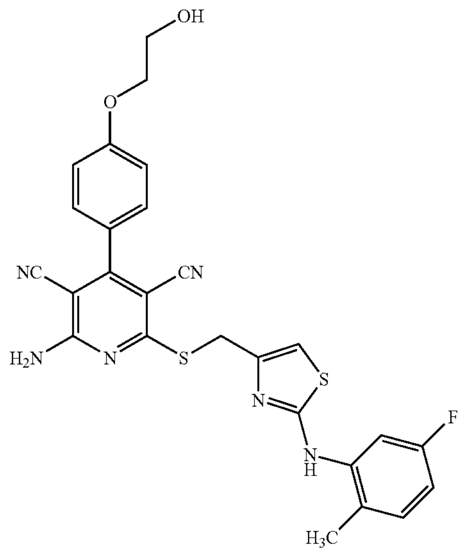 | 533 | 2.35 (2) | 20 |

Example 68

2-(2-Hydroxyethoxy)amino-6-[({2-[(4-fluorophenyl)amino]-1,3-thiazol-4-yl}methyl)thio]-4-[4-(2-hydroxyethoxy)phenyl]pyridine-3,5-dicarbonitrile

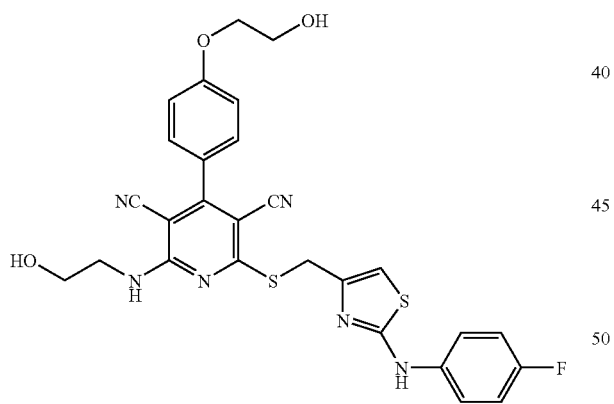

Analogously to Example 8, the title compound is obtained by reacting 120 mg (0.70 mmol) of 4-fluorophenylthiourea with 89 mg (0.70 mmol) of 1,3-dichloroacetone in ethanol, followed by reaction with 245 mg (0.50 mmol) of 2-(2-hydroxyethoxy)amino-4-[4-(2-hydroxyethoxy)phenyl]-6-mercaptopyridine-3,5-dicarbonitrile (Example 32A).

Yield: 30 mg (11% of theory)

$^1$H-NMR (400 MHz, DMSO-d$_6$): δ=10.24 (s, 1H), 8.03 (t, 1H), 7.61 (dd, 2H), 7.46 (d, 2H), 7.12 (m, 4H), 6.81 (s, 1H), 4.91 (t, 1H), 4.80 (t, 1H), 4.50 (s, 2H), 4.07 (t, 2H), 3.74 (dt, 2H), 3.62 (t, 2H), 3.56 (m, 2H).

LC-MS (Method 3): R$_t$=2.10 min; MS (ESIpos): m/z=563 [M+H]$^+$.

Example 69

2-Amino-6-[({2-[(4-cyanophenyl)amino]-1,3-thiazol-4-yl}methyl)thio]-4-{4-[2-(dimethylamino)ethoxy]phenyl}pyridine-3,5-dicarbonitrile

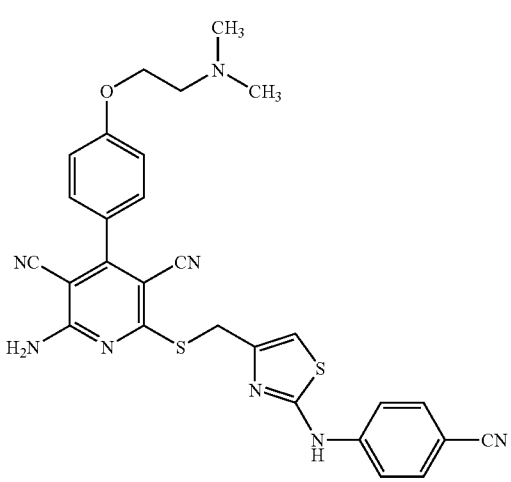

A solution of 26.6 mg (0.15 mmol) of N-(4-cyanophenyl)thiourea and 19 mg (0.15 mmol) of 1,3-dichloroacetone in 0.4 ml of DMF is stirred at +80° C. for 3 h. After cooling to RT, a solution of 50.9 mg (0.15 mmol) of the compound from Example 34A in 0.2 ml of DMF and 50 mg (0.6 mmol) of sodium bicarbonate are added. The mixture is then stirred at RT for 12 h. The reaction mixture is filtered and purified directly by preparative HPLC (column: Macherey Nagel VP50/21 Nucleosil 100-5 C18 Nautilus, 5 μm, 21 mm×50 mm; wavelength: 220 nm; flow rate: 25 ml/min; mobile phase A=water+0.1% formic acid, mobile phase B=acetonitrile; gradient: 0 min 10% B→2 min 10% B→6 min 90% B→7 min 90% B→7.1 min 10% B→8 min 10% B). The product-containing fractions are combined and concentrated using a rotary evaporator.

Yield: 50 mg (57% of theory)

$^1$H-NMR (400 MHz, DMSO-$d_6$): δ=10.80 (s, 1H), 8.17 (s, 1H), 8.20-7.96 (br. s, 2H), 7.82-7.70 (m, 4H), 7.47 (d, 2H), 7.13 (d, 2H), 7.10 (s, 1H), 4.50 (s, 2H), 4.16 (t, 2H), 2.73 (t, 2H), 2.30 (s, 6H).

LC-MS (Method 4): $R_t$=1.87 min; MS (ESIpos): m/z=553 [M+H]$^+$.

Example 70

2-Amino-4-[4-(2-aminoethoxy)phenyl]-6-[({2-[(4-fluorophenyl)amino]-1,3-thiazol-4-yl}methyl)-thio]pyridine-3,5-dicarbonitrile hydrochloride

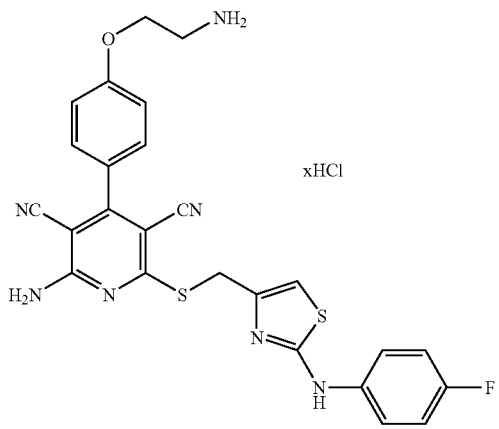

1000 mg (1.84 mmol) of the compound from Example 39A are dissolved in 100 ml of dioxane, 150 mg (1.41 mmol) of palladium-on-activated carbon are added and the mixture is hydrogenated with hydrogen at 3 bar. After 3 h, 4 ml of 2M hydrochloric acid are added and the mixture is hydrogenated with hydrogen at 3 bar for a further 20 h. The mixture is then filtered off with suction through a Seitz clarifying sheet filter, the product is then washed with 50 ml of dioxane, and 50 ml of toluene are added to the filtrate. After removal of the solvent on a rotary evaporator, the residue is taken up in a mixture of 50 ml of water and 50 ml of ethyl acetate. By cautious addition of aqueous dilute sodium bicarbonate solution, the pH is adjusted to about pH 9. The phases formed are separated. The organic phase is dried over magnesium sulphate, the solvent is then removed using a rotary evaporator and the residue is purified by preparative HPLC (column: YMC GEL ODS-AQ S-5/15 μm; mobile phase gradient: acetonitrile/water 10:90→95:5, with addition of 0.5% concentrated hydrochloric acid). The product-containing fractions are combined and concentrated using a rotary evaporator.

Yield: 57 mg (6% of theory)

$^1$H-NMR (400 MHz, DMSO-$d_6$): δ=10.27 (s, 1H), 8.08-7.97 (br. s, 2H), 7.67-7.59 (m, 2H), 7.51 (d, 2H), 7.20-7.09 (m, 4H), 6.98 (s, 1H), 4.47 (s, 2H), 4.25 (t, 2H), 3.31-3.21 (m, 2H).

LC-MS (Method 2): $R_t$=2.08 min; MS (ESIpos): m/z=518 [M+H]$^+$.

Example 71

2-Amino-6-[({2-[(4-fluorophenyl)amino]-1,3-thiazol-4-yl}methyl)thio]-4-[4-(2-hydroxypropoxy)-phenyl]pyridine-3,5-dicarbonitrile

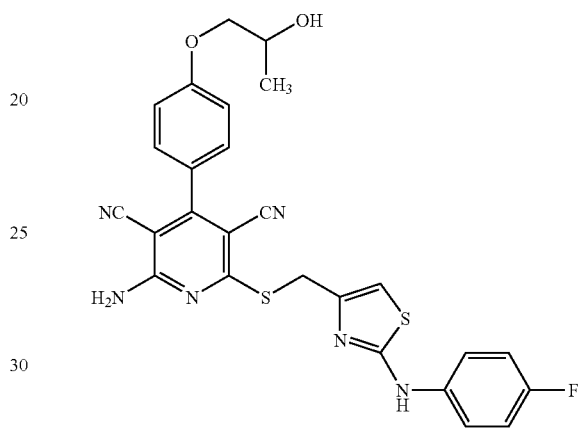

3 ml of 1M hydrochloric acid are added to a solution of 43 mg (0.06 mmol) of the compound from Example 43A in 6 ml of methanol, and the mixture is stirred at RT for 20 h. 10 ml of saturated sodium bicarbonate solution are then added, and the reaction mixture is extracted with ethyl acetate (three times, 10 ml each). The combined organic phases are dried over magnesium sulphate. After removal of the solvent on a rotary evaporator, the crude product is purified chromatographically on silica gel 60 (mobile phase gradient dichloromethane/ethanol 100:1→20:1).

Yield: 0.34 g (96% of theory)

$^1$H-NMR (400 MHz, DMSO-$d_6$): δ=10.22 (s, 1H), 8.22-7.91 (br. s, 2H), 7.61 (dd, 2H), 7.47 (d, 2H), 7.18-7.06 (m, 4H), 6.97 (s, 1H), 4.91 (d, 1H), 4.46 (s, 2H), 4.02-3.94 (m, 1H), 3.94-3.83 (m, 2H), 1.17 (d, 3H).

LC-MS (Method 3): $R_t$=2.26 min; MS (ESIpos): m/z=533 [M+H]$^+$.

B. Assessing the Pharmacological and Physiological Activity

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (foetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $1.1 \times 10^{-11}$M to $3 \times 10^{-6}$M (final concentration). 10 minutes later, forskolin is added to the A1 cells and all the cultures are subsequently incubated at 37° C. for four hours. After that, 35 μl of a solution which is composed of 50% lysis reagent (30 mM disodium hydrogenphosphate, 10% glycerol, 3% TritonX100, 25 mM Tris HCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357 (1998), 1-9].

Table 1 below lists the $EC_{50}$ values of representative working examples for the receptor stimulation on adenosine A1, A2a and A2b receptor subtypes:

TABLE 1

| Example No. | $EC_{50}$ A1 [nM] (1 μM forskolin) | $EC_{50}$ A2a [nM] | $EC_{50}$ A2b [nM] |
|---|---|---|---|
| 2 | 9.9 | 747 | 6.1 |
| 8 | 1 | 300 | 1 |
| 10 | 2 | >200 | 1 |
| 13 | 0.2 | 236 | 0.1 |
| 21 | 0.7 | 103 | 0.5 |

TABLE 1-continued

| Example No. | $EC_{50}$ A1 [nM] (1 μM forskolin) | $EC_{50}$ A2a [nM] | $EC_{50}$ A2b [nM] |
|---|---|---|---|
| 26 | 23 | >3000 | 74 |
| 35 | 0.4 | 142 | 0.3 |
| 39 | 0.3 | 1200 | 1.4 |
| 44 | 0.6 | 140 | 0.3 |
| 48 | 0.4 | 140 | 0.1 |
| 70 | 2.3 | >3000 | 28 |

B-2. Studies on Isolated Blood Vessels

The caudal artery of anaesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Studies on the Langendorff Heart

The heart is rapidly removed after opening the chest cavity of anaesthetized rats and is introduced into a conventional Langendorff apparatus. The coronary arteries are subjected to constant-volume (10 ml/min) perfusion, and the perfusion pressure rising thereby is recorded via an appropriate pressure transducer. A decrease in the perfusion pressure in this arrangement corresponds to a relaxation of the coronary arteries. At the same time, the pressure developed by the heart during each contraction is measured via a balloon introduced into the left ventricle, and a further pressure transducer. The rate at which the isolated heart beats is found by calculation from the number of contractions per unit time.

B4. Measurement of Blood Pressure and Heart Rate on Awake Rats

Various dosages of test substances are administered orally to awake SHR (spontaneously hypertensive rats) rats carrying an internal transmitter capable of measuring permanently both blood pressure and heart rate (telemetric monitoring of haemodynamic parameters. Blood pressure, heart rate and their changes are then recorded over a period of 24 hours.

B-5. Measurement of Blood Pressure and Heart Rate on Awake Rhesus Monkeys and Marmosets Awake rhesus monkeys are fixed in a tube. For the infusion of test substances and for taking blood samples, catheters are placed into the veins of the legs of the animals. At various concentrations, test substances are infused intravenously via one of the catheters over a period of 15-30 minutes. Changes in blood pressure and heart rate are monitored every 1-5 minutes for a total of 60 minutes, using a commercially available instrument for measuring the blood pressure of premature babies. For this purpose, the measuring sleeve is fixed on one of the legs.

Various concentrations of the test substances are administered orally to awake marmosets which carry an internal transmitter capable of measuring both blood pressure and heart rate (telemetric monitoring of haemodynamic parameters). Blood pressure, heart rate and their changes are then recorded for a period of 6-24 hours.

C. Working Examples of Pharmaceutical Compositions

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

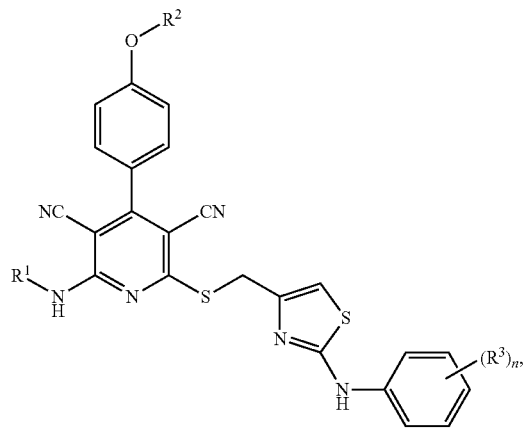

in which $R^1$ represents hydrogen or represents $(C_1-C_6)$-alkyl which may be substituted by hydroxyl, amino, or mono- or di-$(C_1-C_4)$-alkylamino, $R^2$ represents $(C_2-C_6)$-alkyl which is mono- or disubstituted by identical or different substituents selected from the group consisting of hydroxyl, $(C_1-C_4)$-alkoxy, amino, mono- and di-$(C_1-C_4)$-alkylamino, $R^3$ represents a substituent selected from the group consisting of halogen, cyano, nitro, $(C_1-C_6)$-alkyl, hydroxyl, $(C_1-C_6)$-alkoxy, amino, mono- and di-$(C_1-C_6)$-alkylamino, carboxyl and $(C_1-C_6)$-alkoxycarbonyl, where alkyl and alkoxy for their part may in each case be substituted up to five times by fluorine, and n represents the number 0, 1, 2, 3, 4 or 5, where, if the substituent $R^3$ is present more than once, its meanings may be identical or different, or a salt, thereof.

2. The compound of formula (I) according to claim 1, in which $R^1$ represents hydrogen or represents $(C_1-C_4)$-alkyl which may be substituted by hydroxyl, amino or dimethylamino, $R^2$ represents $(C_2-C_4)$-alkyl which is mono- or disubstituted by identical or different substituents selected from the group consisting of hydroxyl, methoxy and amino, $R^3$ represents a substituent selected from the group consisting of halogen, cyano, nitro, $(C_1-C_4)$-alkyl, hydroxyl, $(C_1-C_4)$-alkoxy, amino, mono- and di-$(C_1-C_4)$-alkylamino, carboxyl and $(C_1-C_4)$-alkoxycarbonyl, where alkyl and alkoxyl for their part may in each case be substituted up to three times by fluorine, and n represents the number 0, 1 or 2, where, if the substituent $R^3$ is present twice, its meanings may be identical or different.

3. The compound of formula (I) according to claim 1, in which $R^1$ represents hydrogen, $R^2$ represents ethyl, n-propyl or isopropyl which are in each case mono- or disubstituted by identical or different substituents selected from the group consisting of hydroxyl, methoxy and amino, $R^3$ represents a substituent selected from the group consisting of fluorine, chlorine, bromine, cyano, nitro, methyl, ethyl, trifluoromethyl, hydroxyl, methoxy, ethoxy, amino, mono- and dimethylamino, carboxyl, methoxycarbonyl and ethoxycarbonyl, and n represents the number 0, 1 or 2, where, if the substituent $R^3$ is present twice, its meanings may be identical or different.

4. A pharmaceutical composition comprising a compound according to claim 1 and an inert, nontoxic, pharmaceutically suitable auxiliary.

\* \* \* \* \*

UNITED STATES PATENT AND TRADEMARK OFFICE
CERTIFICATE OF CORRECTION

| | | |
|---|---|---|
| PATENT NO. | : 8,691,850 B2 | Page 1 of 1 |
| APPLICATION NO. | : 11/661820 | |
| DATED | : April 8, 2014 | |
| INVENTOR(S) | : Erguden et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1119 days.

Signed and Sealed this
Twenty-first Day of July, 2015

Michelle K. Lee
*Director of the United States Patent and Trademark Office*